(12) United States Patent
Cummings

(10) Patent No.: US 11,813,016 B2
(45) Date of Patent: Nov. 14, 2023

(54) ELECTROSURGICAL SHEARS WITH THUMB RING KNIFE ACTUATOR

(71) Applicant: Cilag GmbH International, Zug (CH)

(72) Inventor: Nathan Cummings, Blue Ash, OH (US)

(73) Assignee: Cilag GmbH International, Zug (CH)

( * ) Notice: Subject to any disclaimer, the term of this patent is extended or adjusted under 35 U.S.C. 154(b) by 753 days.

(21) Appl. No.: 16/033,253

(22) Filed: Jul. 12, 2018

(65) Prior Publication Data
US 2020/0015881 A1    Jan. 16, 2020

(51) Int. Cl.
*A61B 18/14* (2006.01)
*A61B 18/00* (2006.01)
*A61B 18/12* (2006.01)

(52) U.S. Cl.
CPC ...... *A61B 18/1445* (2013.01); *A61B 18/1206* (2013.01); *A61B 2018/0063* (2013.01); *A61B 2018/00601* (2013.01); *A61B 2018/126* (2013.01); *A61B 2018/1405* (2013.01); *A61B 2018/1455* (2013.01)

(58) Field of Classification Search
CPC ..... A61F 7/007; A61F 7/02; A61F 2007/0094
See application file for complete search history.

(56) References Cited

U.S. PATENT DOCUMENTS

| 6,500,176 B1 | 12/2002 | Truckai et al. |
|---|---|---|
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 8,939,974 B2 | 1/2015 | Boudreaux et al. |
| 9,089,327 B2 | 7/2015 | Worrell et al. |

(Continued)

OTHER PUBLICATIONS

U.S. Appl. No. 15/989,424, entitled "Method and Apparatus for Open Electrosurgical Shears," filed May 25, 2018.

(Continued)

*Primary Examiner* — Joseph A Stoklosa
*Assistant Examiner* — Annie L Shoulders
(74) *Attorney, Agent, or Firm* — Frost Brown Todd LLP

(57) ABSTRACT

A surgical instrument includes an end effector, a handle assembly, and a firing assembly. The end effector includes a first jaw, a second jaw, a knife, and an electrode assembly. The second jaw pivot between an open position and a closed position. The handle assembly includes a housing associated with the first jaw and an arm associated with the second jaw. The arm can pivot the second jaw between the open position and the closed position. The firing assembly can actuate the knife between a pre-fired position and a fired position. The firing assembly includes a first body slidably attached to the housing and a second body slidably attached to the arm. The second body couples with the first body when the second jaw is in the closed position. The second body decouples with the first body when the second jaw is in the open position.

13 Claims, 21 Drawing Sheets

(56) References Cited

U.S. PATENT DOCUMENTS

| | | |
|---|---|---|
| 9,161,803 B2 | 10/2015 | Yates et al. |
| 9,402,682 B2 | 8/2016 | Worrell et al. |
| 9,545,253 B2 | 1/2017 | Worrell et al. |
| 9,610,114 B2 | 4/2017 | Baxter, III et al. |
| 9,717,485 B1* | 8/2017 | Doerr .................. A61B 17/00 |
| 9,877,720 B2 | 1/2018 | Worrell et al. |
| 2009/0182327 A1* | 7/2009 | Unger ................ A61B 18/1445 606/46 |
| 2012/0083783 A1* | 4/2012 | Davison ............. A61B 18/1445 606/45 |
| 2014/0276770 A1* | 9/2014 | Ellman .............. A61B 18/1477 606/34 |
| 2014/0358142 A1* | 12/2014 | Miller ................ A61B 18/1447 606/47 |
| 2016/0175030 A1* | 6/2016 | Boudreaux ........ A61B 18/1442 606/42 |
| 2016/0270780 A1* | 9/2016 | Hall ....................... A61B 34/74 |

OTHER PUBLICATIONS

U.S. Appl. No. 15/989,436, entitled "Electrosurgical Shears with Knife Lock and Clamp-Actuated Switch," filed May 25, 2018.

U.S. Appl. No. 15/989,433, entitled "knife Drive Assembly for Electrosurgical Shears," filed May 25, 2018.

U.S. Appl. No. 15/989,438, entitled "knife Auto-Return Assembly for Electrosurgical Shears," filed May 25, 2018.

U.S. Appl. No. 15/989,442, entitled "Compound Screw Knife Drive for Electrosurgical Shears," filed May 25, 2018.

U.S. Appl. No. 15/989,448, entitled "Firing and Lockout Assembly for Knife for Electrosurgical Shears," filed May 25, 2018.

U.S. Appl. No. 15/989,452, entitled "Dual State Energy Activation for Electrosurgical Shears," filed May 25, 2018.

U.S. Appl. No. 15/989,455, entitled "Latching Clamp Arm for Electrosurgical Shears," filed May 25, 2018.

\* cited by examiner

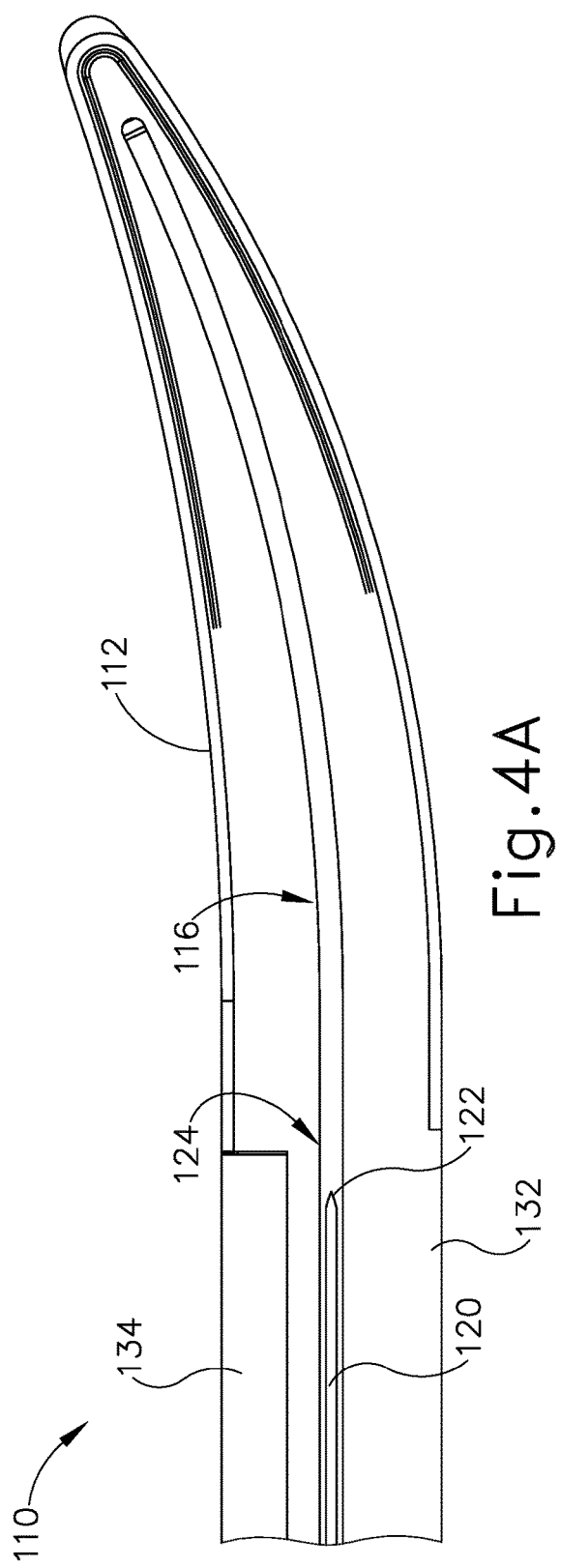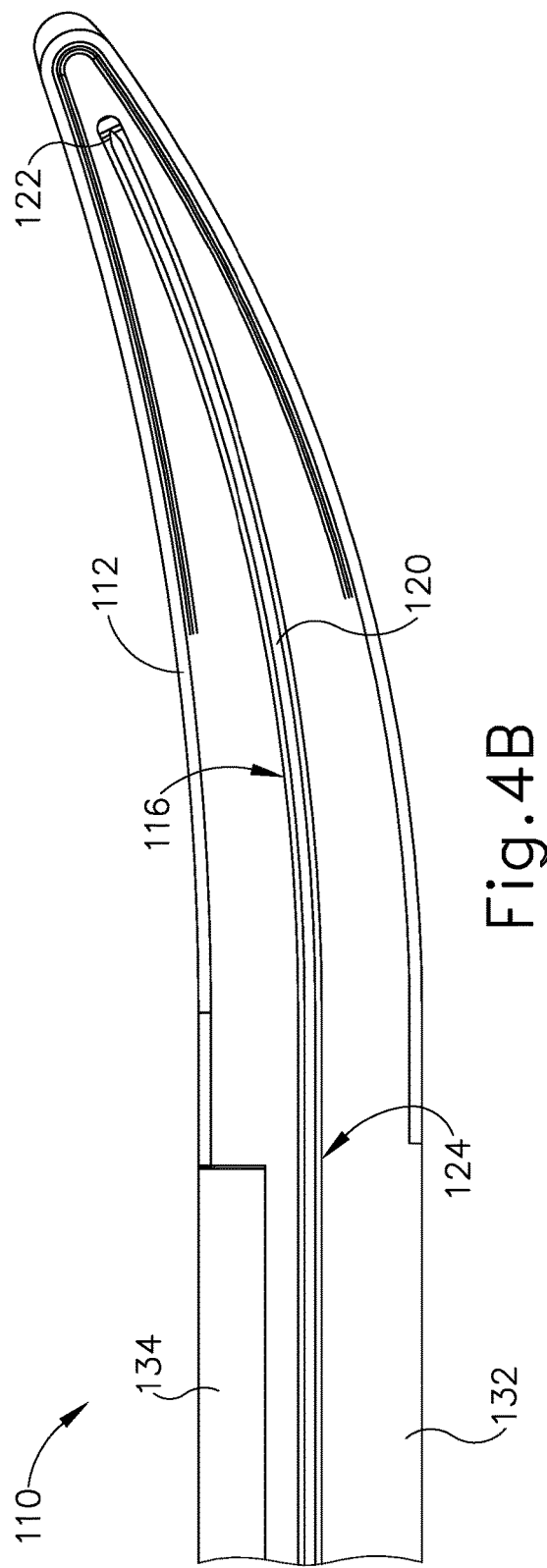

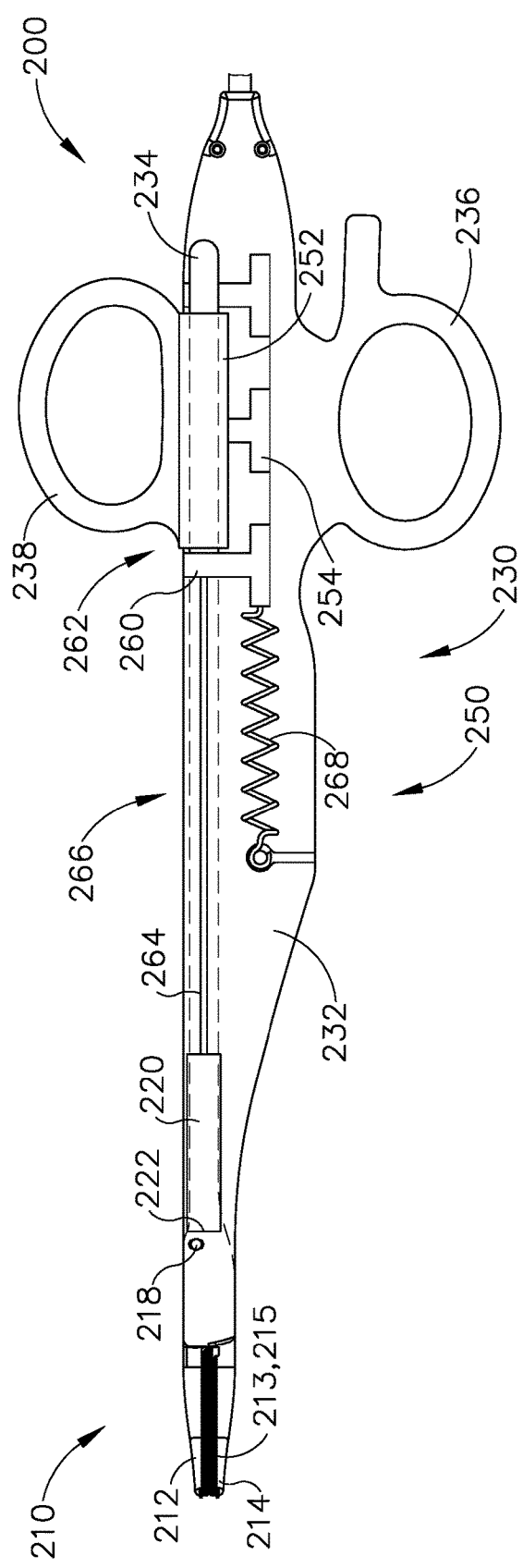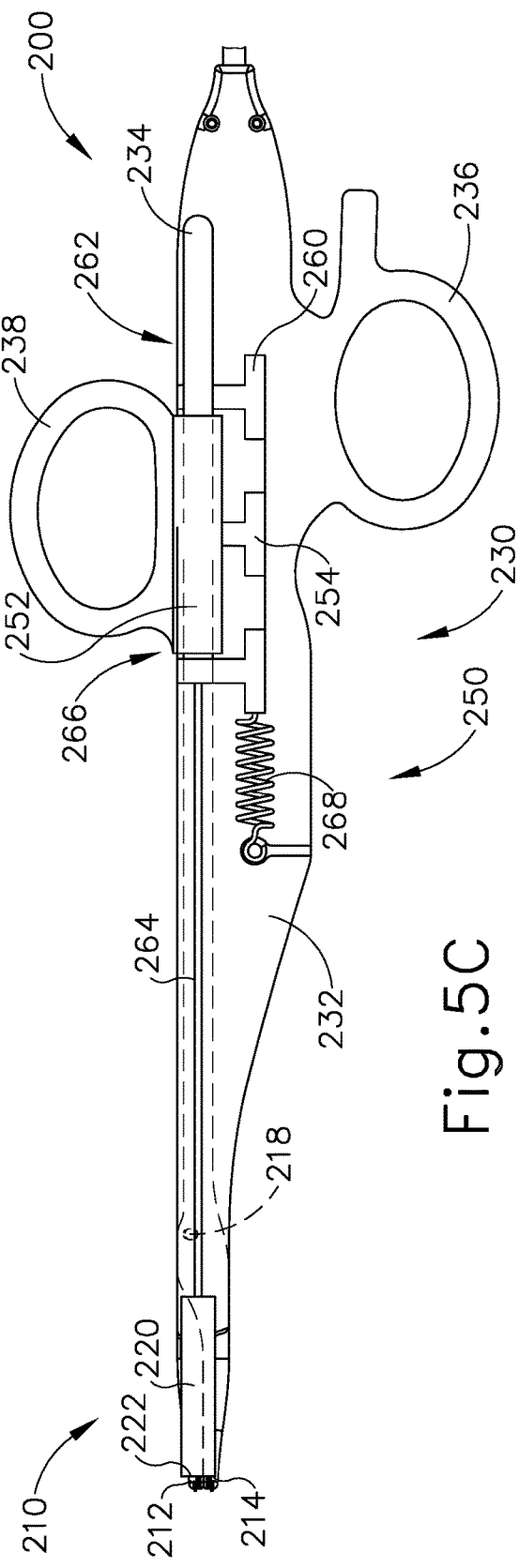
Fig.5B
Fig.5C

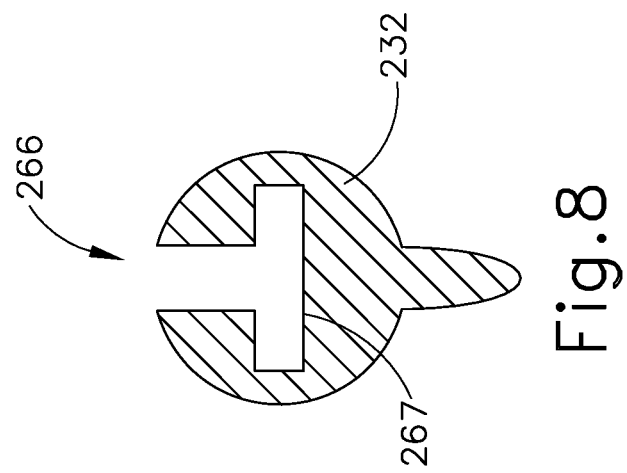
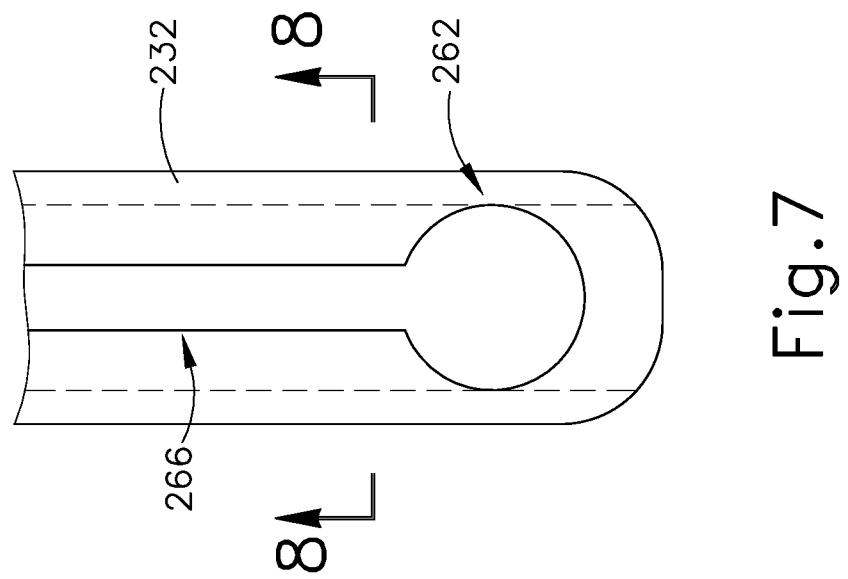

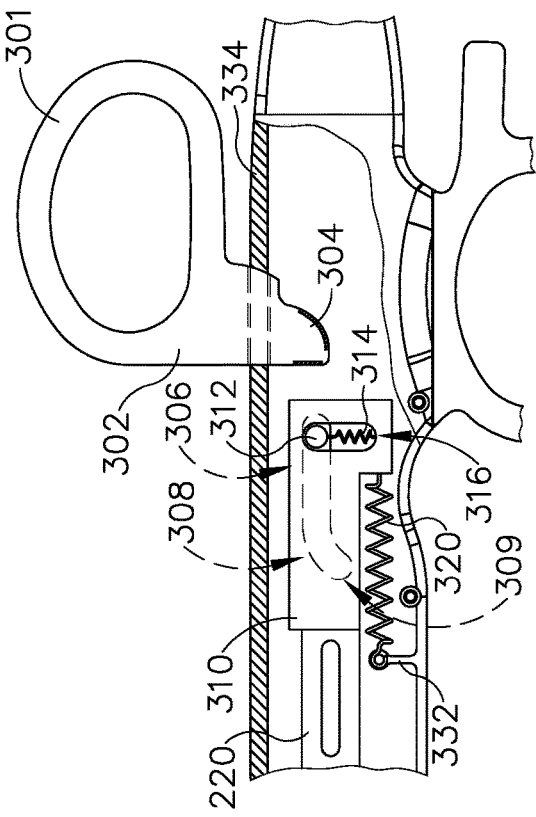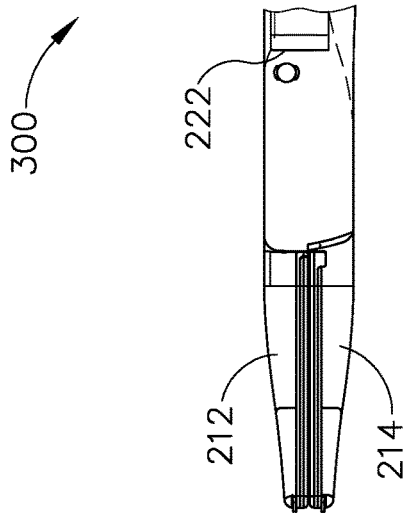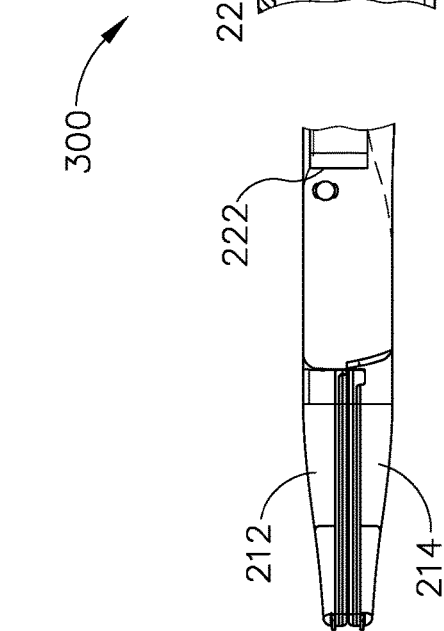

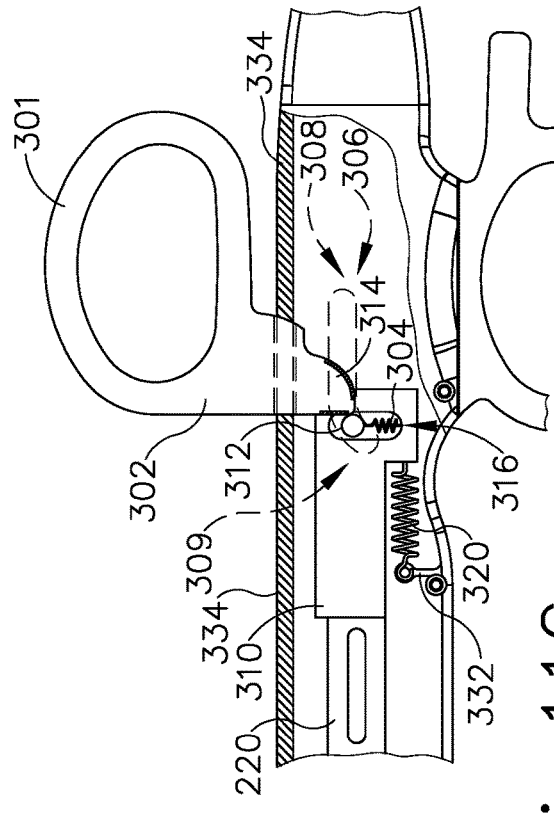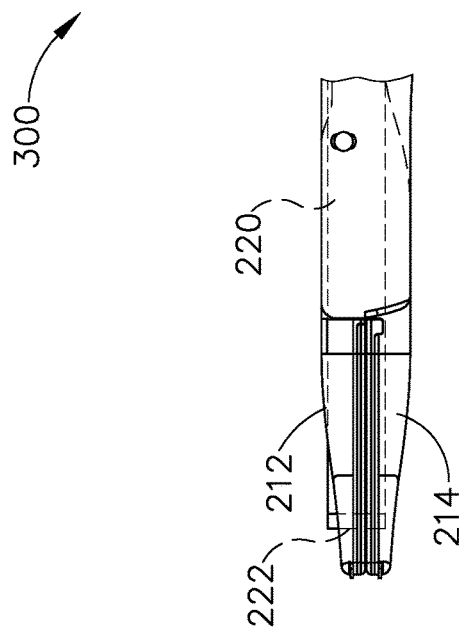
Fig.11C
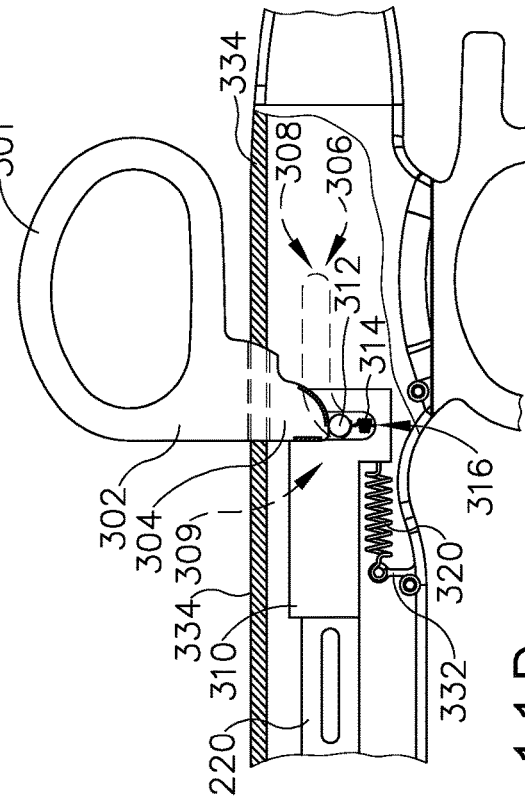
Fig.11D

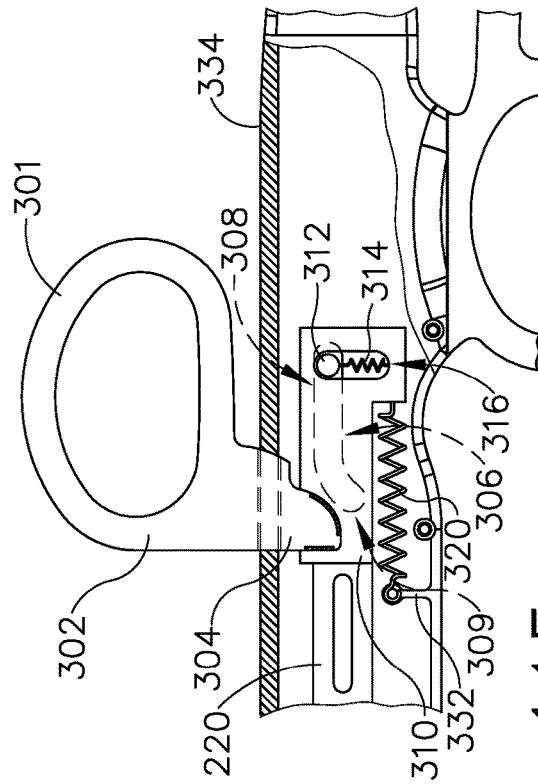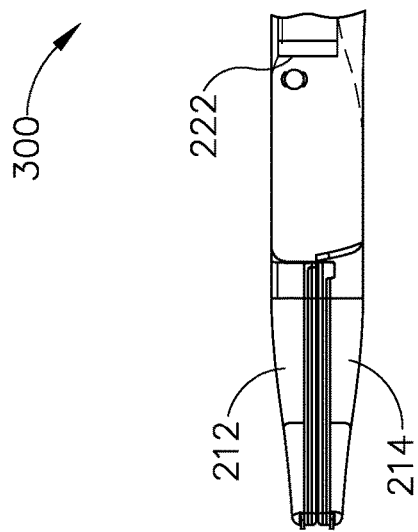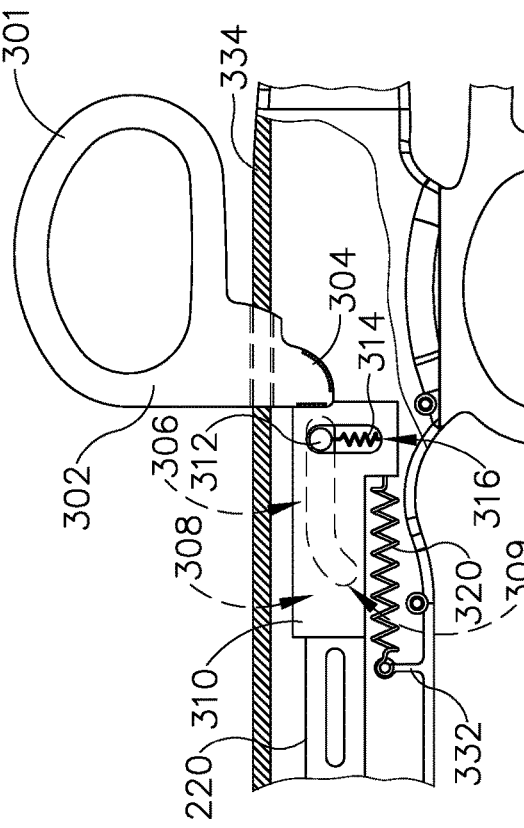

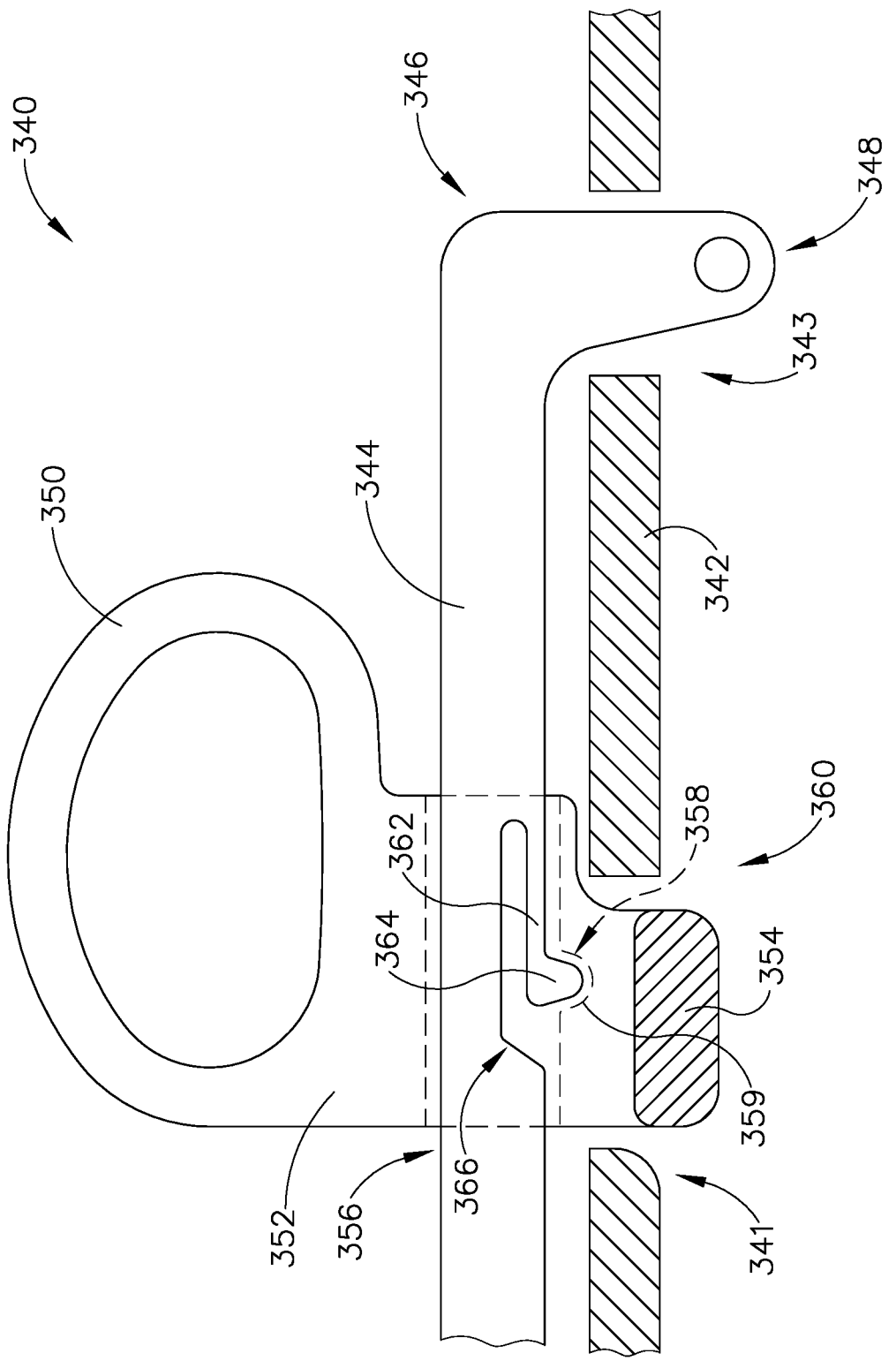

ELECTROSURGICAL SHEARS WITH THUMB RING KNIFE ACTUATOR

BACKGROUND

A variety of surgical instruments include one or more elements that transmit RF energy to tissue (e.g., to coagulate or seal the tissue). Some such instruments comprise a pair of jaws that open and close on tissue, with conductive tissue contact surfaces that are operable to weld tissue clamped between the jaws. In open surgical settings, some such instruments may be in the form of forceps having a scissor grip.

In addition to having RF energy transmission elements, some surgical instruments also include a translating tissue cutting element. An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pat. No. 9,877,720, entitled "Control Features for Articulating Surgical Device," issued Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; and U.S. Pat. No. 9,545,253, entitled "Surgical Instrument with Contained Dual Helix Actuator Assembly," issued Jan. 17, 2017, the disclosure of which is incorporated by reference herein.

Some versions of electrosurgical instruments that are operable to sever tissue may be selectively used in at least two modes. One such mode may include both severing tissue and coagulating tissue. Another such mode may include just coagulating tissue without also severing the tissue. Yet another mode may include the use of jaws to grasp and manipulate tissue without also coagulating and/or severing the tissue. When an instrument includes grasping jaws and tissue severing capabilities, the instrument may also include a feature that ensures full closure of the jaws before the tissue is severed and/or before the electrodes are activated.

While various kinds of surgical instrument have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4A depicts a cross-sectional view of the end effector of FIG. 1, taken along line 4-4 of FIG. 1, where the translating knife of FIG. 2 is in the proximal position;

FIG. 4B depicts a cross-sectional view of the end effector of FIG. 1, taken along line 4-4 of FIG. 1, where the translating knife of FIG. 2 is in the distal position;

FIG. 5B depicts an elevational side view of the electrosurgical forceps instrument of FIG. 5A, with some internal components show schematically, where the end effector is in a closed position, where the firing assembly is in the pre-fired position;

FIG. 5C depicts an elevational side view of the electrosurgical forceps instrument of FIG. 5A, with some internal components show schematically, where the end effector is in the closed position, where the firing assembly is in a fired position;

FIG. 7 depicts a top plan view of a housing of the electrosurgical forceps instrument of FIG. 5A;

FIG. 8 depicts a cross-sectional view, taken along line 8-8 of FIG. 7, of the housing of FIG. 7;

FIG. 11A depicts a side elevational view of an alternative firing assembly that may be readily incorporated into the electrosurgical forceps instrument of FIG. 5A, with some instrument components shown in cross-section and other shown schematically, where the firing assembly is in a first pre-fired position;

FIG. 11B depicts a side elevational view of the firing assembly of FIG. 11A, with some instrument components shown in cross-section and other shown schematically, where the firing assembly is in a second pre-fired position;

FIG. 11C depicts a side elevational view of the firing assembly of FIG. 11A, with some instrument components shown in cross-section and other shown schematically, where the firing assembly is in a first fired position;

FIG. 11D depicts a side elevational view of the firing assembly of FIG. 11A, with some instrument components shown in cross-section and other shown schematically, where the firing assembly is in a second fired position;

FIG. 11E depicts a side elevational view of the firing assembly of FIG. 11A, with some instrument components shown in cross-section and other shown schematically, where the firing assembly is in a pre-returned, post-fired position;

FIG. 11F depicts a side elevational view of the firing assembly of FIG. 11A, with some instrument components shown in cross-section and other shown schematically, where the firing assembly is returned to the pre-fired position;

FIG. 12 depicts a side elevational view of an exemplary handle assembly having a thumb ring latch assembly that may be readily incorporated into the electrosurgical forceps instrument of FIG. 5A, with some instrument components shown in cross-section;

DETAILED DESCRIPTION

Figure 1:
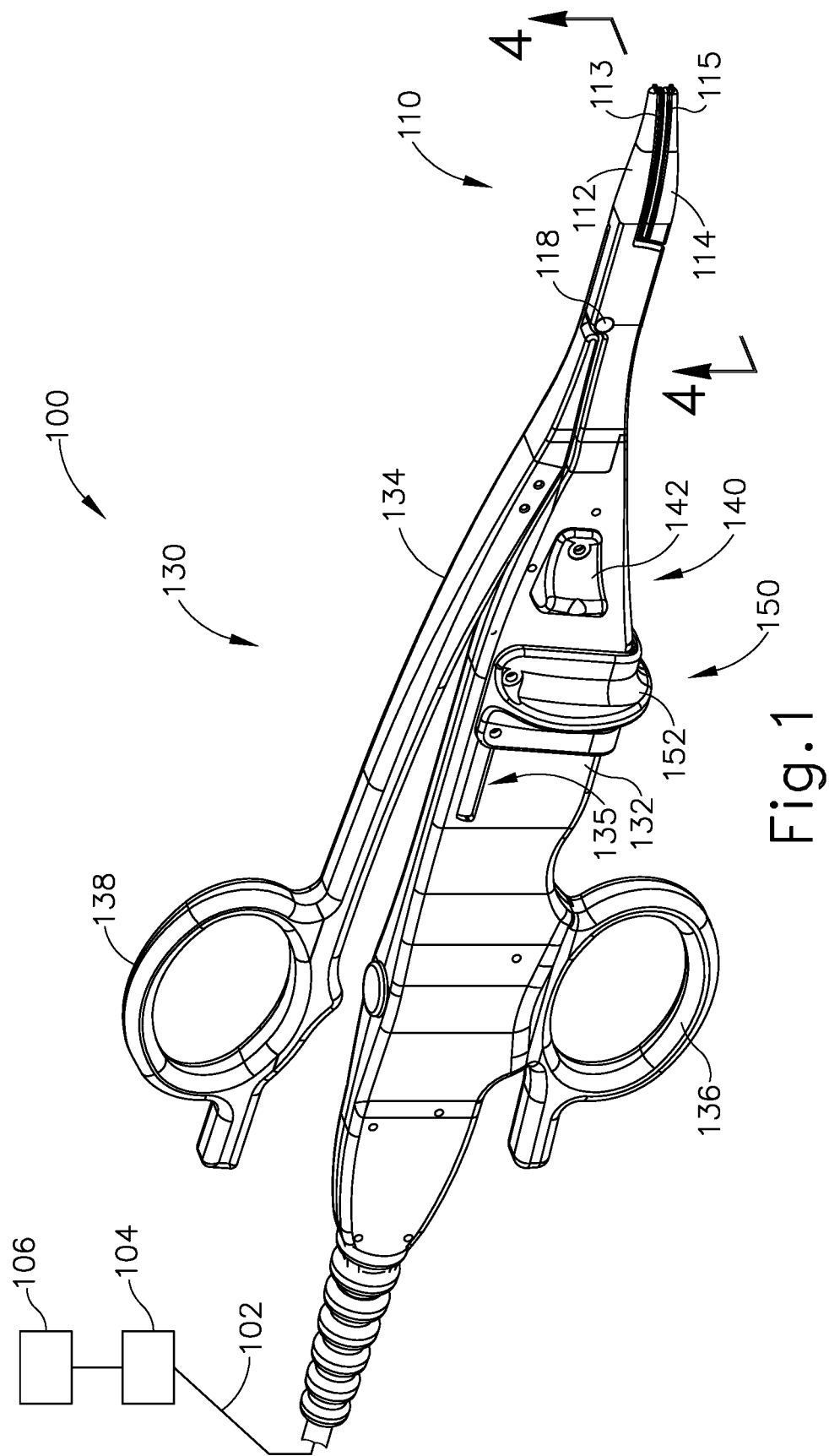
FIG. 1 depicts a perspective view of an exemplary electrosurgical forceps instrument, where an end effector is in a closed position, where a resilient arm is in a relaxed position.
Figure 2:
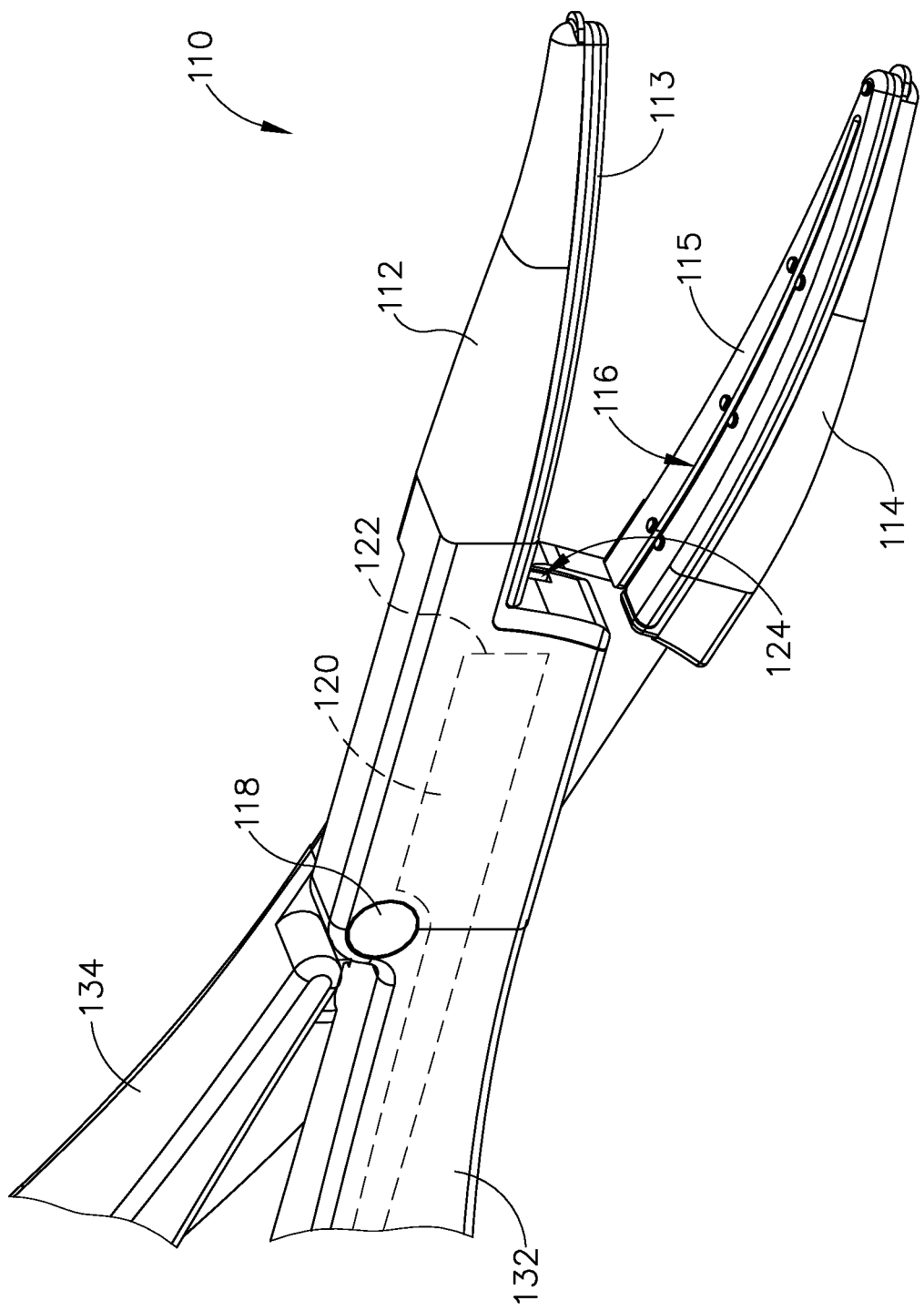
FIG. 2 depicts a perspective view of the end effector of FIG. 1 in an opened position, where a translating knife is in a proximal position.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Electrosurgical Forceps

As previously noted, an electrosurgical instrument may include a set of jaws, with at least one of the jaws being pivotable relative to the other jaw to selectively compress tissue between the jaws. Once the tissue is compressed, electrodes in the jaws may be activated with bipolar RF energy to seal the tissue. In some instances, a cutting feature is operable to sever tissue that is clamped between the jaws. For instance, the cutting feature may be actuated before or after the RF energy has sealed the tissue. Various references that are cited herein relate to electrosurgical instruments where the jaws are part of an end effector at the distal end of an elongate shaft, such that the end effector and the shaft may be inserted through a port (e.g., a trocar) to reach a site within a patient during a minimally invasive endoscopic surgical procedure. A handle assembly may be positioned at the proximal end of the shaft for manipulating the end effector. Such a handle assembly may have a pistol grip configuration or some other configuration.

In some instances, it may be desirable to provide an electrosurgical instrument that does not have an elongate shaft or handle assembly similar to those described in the various references cited herein. In particular, it may be desirable to provide an electrosurgical instrument that is configured similar to a forceps device, with a scissor grip. Such instruments may be used in a variety of medical procedures. Various examples of electrosurgical shears/forceps devices are disclosed in U.S. Pat. No. 9,610,144, entitled "Electrosurgical Hand Shears," filed Jan. 29, 2013, the disclosure of which is incorporated by reference herein. Various other examples of electrosurgical forceps instruments will be described in greater detail below; while other examples will be apparent to those of ordinary skill in the art in view of the teachings herein.

FIGS. 1-4B show an exemplary electrosurgical forceps instrument (100). Instrument (100) includes a handle assembly (130) extending distally into an end effector (110). As will be described in greater detail below, instrument (100) may be used to grasp, seal, and sever tissue captured by end effector (110).

End effector (110) includes a first jaw (112) having a first electrode (113), a second jaw (114) having a second electrode (115), and a knife (120) configured to translate through the first jaw (112) and the second jaw (114). First jaw (112) and second jaw (114) are pivotably coupled with each other via pivot pin (118). First jaw (112) and second jaw (114) may pivot between an open position (FIG. 2) and a closed position (FIG. 1) in order to grasp tissue. First and second electrodes (113, 115) are positioned on respective jaws (112, 114) such that electrodes (113, 115) face each other when jaws (112, 114) are pivoted into the closed position. Additionally, each electrode (113, 115) is U-shaped in the present example, with the bend of the U-shape located near the distal end of each respective jaw (112, 114), such that each electrode (113, 115) includes two longitudinally extending, laterally spaced-apart legs extending along the length of each respective jaw (112, 114). Laterally spaced-apart legs of each electrode (113, 115) and corresponding portions of jaws (112, 114) define an elongate slot (116). Elongate slot (116) is dimensioned to slidably receive knife (120) such that knife (120) may translate from a proximal position (FIG. 4A) to a distal position (FIG. 4B). Knife (120) includes a distal cutting edge (122) configured to sever tissue captured between jaws (112, 114) in the closed position.

A cable (102) extends proximally from handle assembly (130). Cable (102) is coupled with a control unit (104), which is further coupled with a power source (106). Power source (106) may power control unit (104). Control unit (104) is operable to provide RF power to electrodes (113, 115) of jaws (112, 114), to thereby seal tissue suitably captured between jaws (112, 114).

Handle assembly (130) includes a housing (132), and a resilient arm (134). Housing (132) contains an electrode activation assembly (140) and a firing assembly (150). Housing (132) and resilient arm (134) are pivotably coupled with each other via pivot pin (118). Housing (132) extends distally into first jaw (112), while resilient arm (134) extends distally into second jaw (114). Housing (132) defines a knife pathway (124) that slidably houses knife (120). Housing (132) includes a finger ring (136) while resilient arm (134) terminates proximally into a thumb ring (138). Therefore, the operator may grasp instrument (100) in a scissor grip fashion and pivot resilient arm (134) relative to housing (132) via rings (136, 138) in order to open and close jaws (112, 114).

Resilient arm (134) is sufficiently resilient that arm (134) may flex from a relaxed position (FIG. 3B) to a flexed position (FIG. 3C) in response to pivoting arm (134) further toward housing (132) when jaws (112, 114) are already in the closed position. Resilient arm (134) is biased toward the relaxed position. Further pivoting of resilient arm (134) into the flexed position may result in greater closure forces between jaws (112, 114) as compared to pivoting jaws (112, 114) into the closed position while arm (134) is in the relaxed position. Resilient arm (134) may be suitably resilient such that when resilient arm (134) is pivoted into the flexed position, the closure force between jaws (112, 114) is sufficient such that electrodes (113, 115) may properly seal tissue grasped between jaws (112, 114). Additionally, the resilient nature of arm (134) may limit the amount of closure force between jaws (112, 114) such that jaws (112, 114) may not compress tissue too much, resulting in inadvertent tissue damage. When the operator no longer desires to compress tissue between jaws (112, 114) to properly seal clamped tissue, the operator may reduce the amount of closure force applied to resilient arm (134) such that arm (134) returns to the relaxed state.

Housing (132) slidingly supports an RF trigger (142) of electrode activation assembly (140). RF trigger (142) is in communication with control unit (104). RF trigger (142) may be pressed or actuated to command control unit (104) to supply RF energy to electrodes (113, 115) of end effector (110). RF trigger (142) may electrically couple with control unit (104) through any suitable components known to a person having ordinary skill in the art in view of the teachings herein.

As will be described in greater detail below, firing assembly (150) is configured to actuate knife (120) within jaws (112, 114) from a proximal position to a distal position in order to sever tissue captured between jaws (112, 114). Previous firing assemblies for electrosurgical forceps may have had a trigger that was a lever arm configured to rotate relative to a handle assembly to actuate a knife. The lever arm may have extended away from the handle assembly in order to provide a mechanical advantage for actuating knife (120) within jaws (112, 114). However, when lever arm extends away from handle assembly, it may become difficult rotate lever arm when instrument is flipped such that thumb ring becomes finger rings and vice versa. In such instances when instrument is flipped, the lever arm may no longer associate with the index/middle finger for actuating the lever arm.

Therefore, it may be desirable to have a compact firing assembly with a trigger close to the center of housing such that it is easy to actuate firing assembly with the same finger(s), even when instrument is flipped. Firing assembly (150) of the current example includes a knife trigger (152) slidably coupled with housing (132) via a slot (135). Trigger (152) is close to the center of housing (132) such that trigger (152) may be easily accessed regardless if instrument (100) is flipped around. Trigger (152) may actuate relative to housing (132) in order to actuate a knife (120) of end effector (110). In particular, proximal translation of trigger (152) results in distal translation of knife (120), while distal translation of trigger (152) results in proximal translation of knife (120). Trigger (152) may be biased toward the distal position such that knife (120) is biased toward the proximal position.

Trigger (152) may be coupled with knife (120) through any suitably firing mechanism assembly as would be apparent to one having ordinary skill in the art in view of the teachings herein. It should be understood that trigger (152) may be selectively actuated at any suitable time the operator desires. For instance, the operator may grasp tissue by pivoting jaws (112, 114) to the closed position, wait a desired amount of time, and fire trigger (152) to actuate knife (120) and sever tissue. Alternatively, the operator may grasp tissue by pivoting jaws (112, 114), release tissue if jaws (112, 114) are not satisfactorily grasping tissue, re-grasp tissue, and then fire trigger (152) to actuate knife (120) and sever tissue.

Figure 3A:
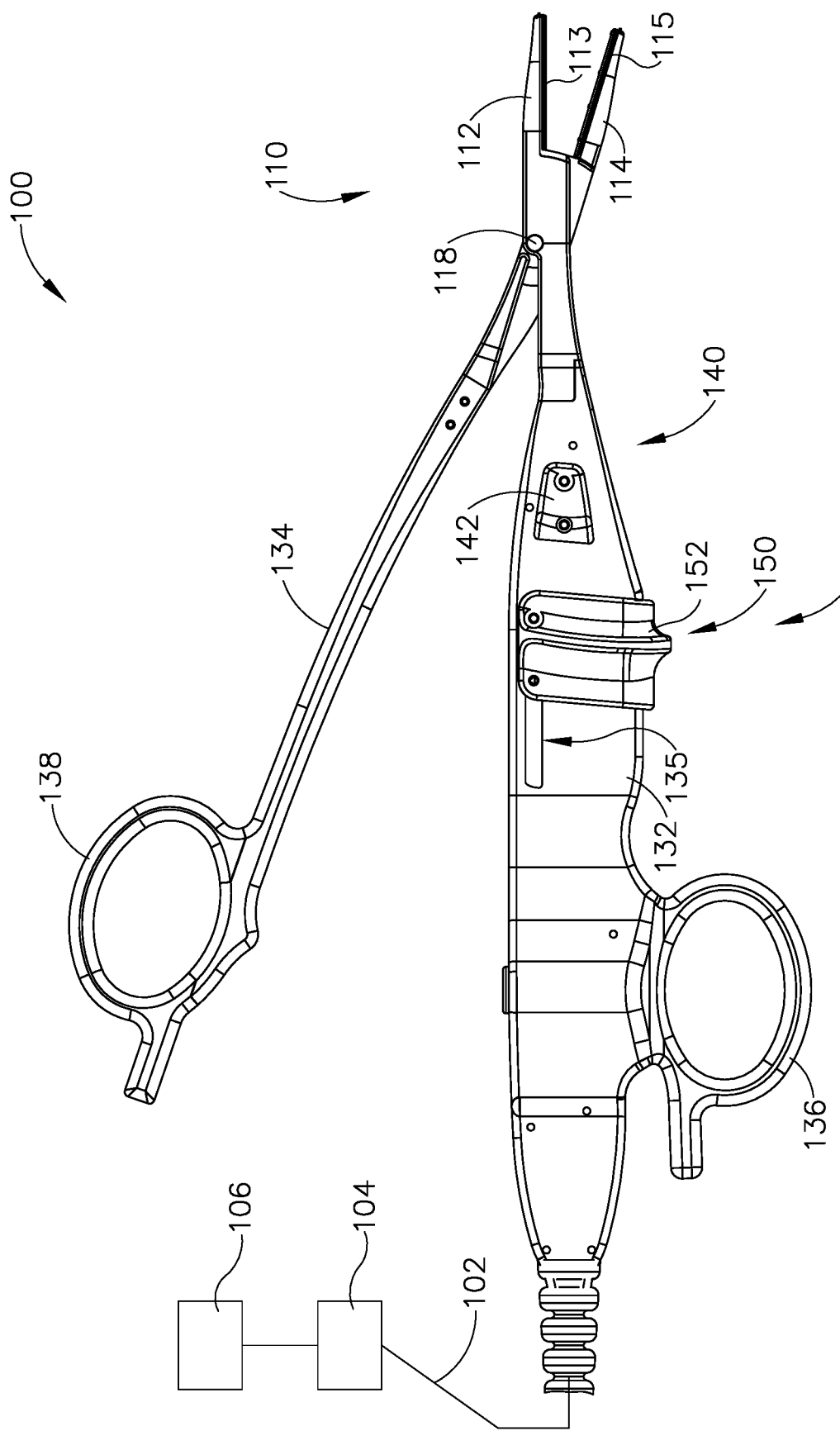
FIG. 3A depicts a side elevational view of the electrosurgical forceps instrument of FIG. 1, where the end effector is in the opened position, where the resilient arm is in the relaxed position, and where the translating knife of FIG. 2 is in the proximal position.
Figure 3B:
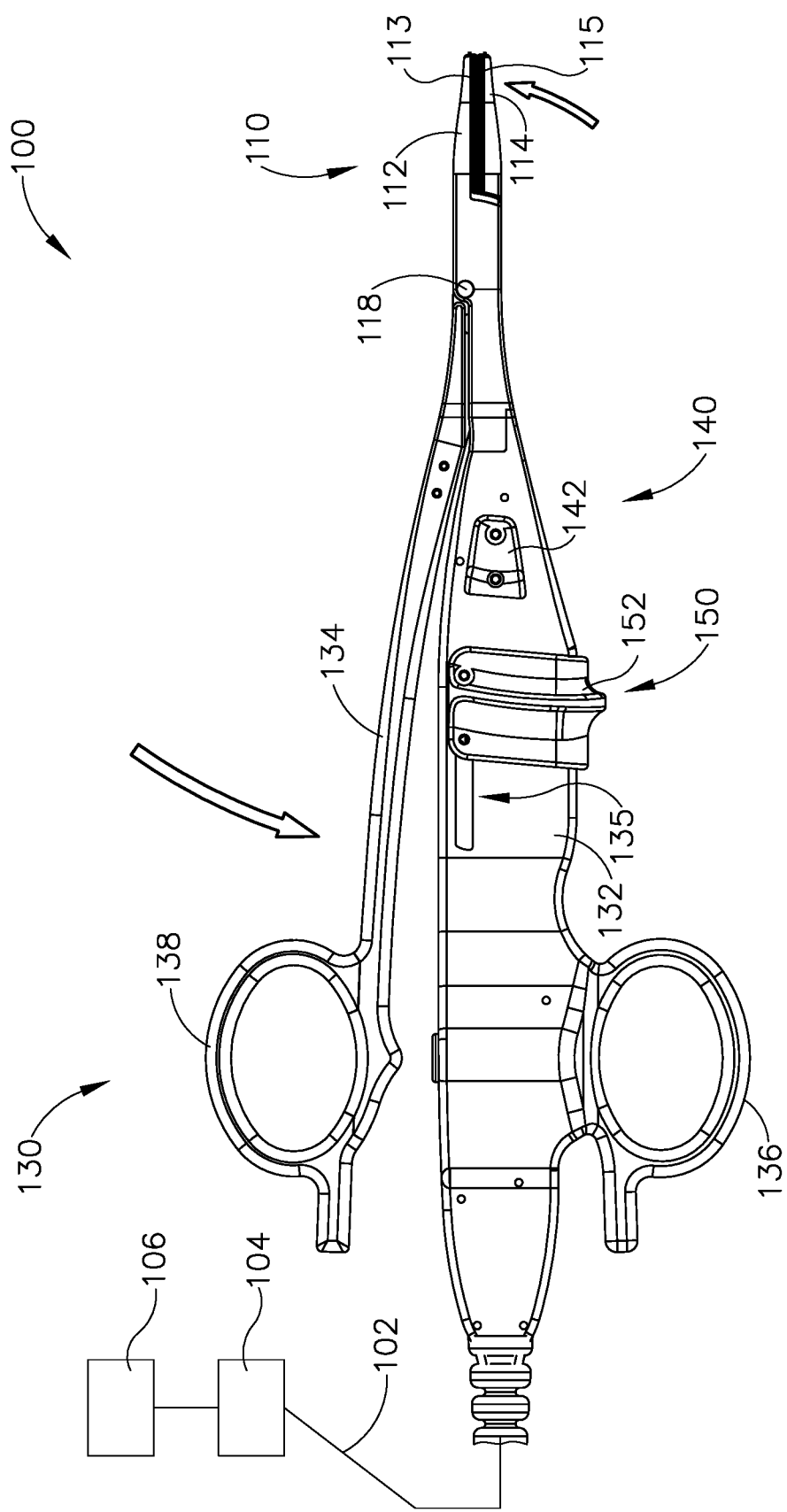
FIG. 3B depicts a side elevational view of the electrosurgical forceps instrument of FIG. 1, where the end effector is in the closed position, where the resilient arm is in the relaxed position, and where the translating knife of FIG. 2 is in the proximal position.

FIGS. 3A-4B show an exemplary operation of instrument (100). FIG. 3A shows jaws (112, 114) of end effector (110) in the opened position. Therefore, resilient arm (134) is pivoted away from housing (132). As shown in FIG. 3B, when the operator desires to initially grasp and manipulate tissue, the operator may pivot resilient arm (134) toward housing (132) such that jaws (112, 114) are pivoted toward the closed position while resilient arm (134) remains in the relaxed position. With jaws (112, 114) pivoted toward the closed position, the operator may manipulate tissue grasped by jaws (112, 114). It should be understood that the closure forces imparted on tissue by jaws (112, 114) at this point may not be sufficient enough for suitable sealing of tissue via RF energy provided by electrodes (113, 115).

Figure 3C:
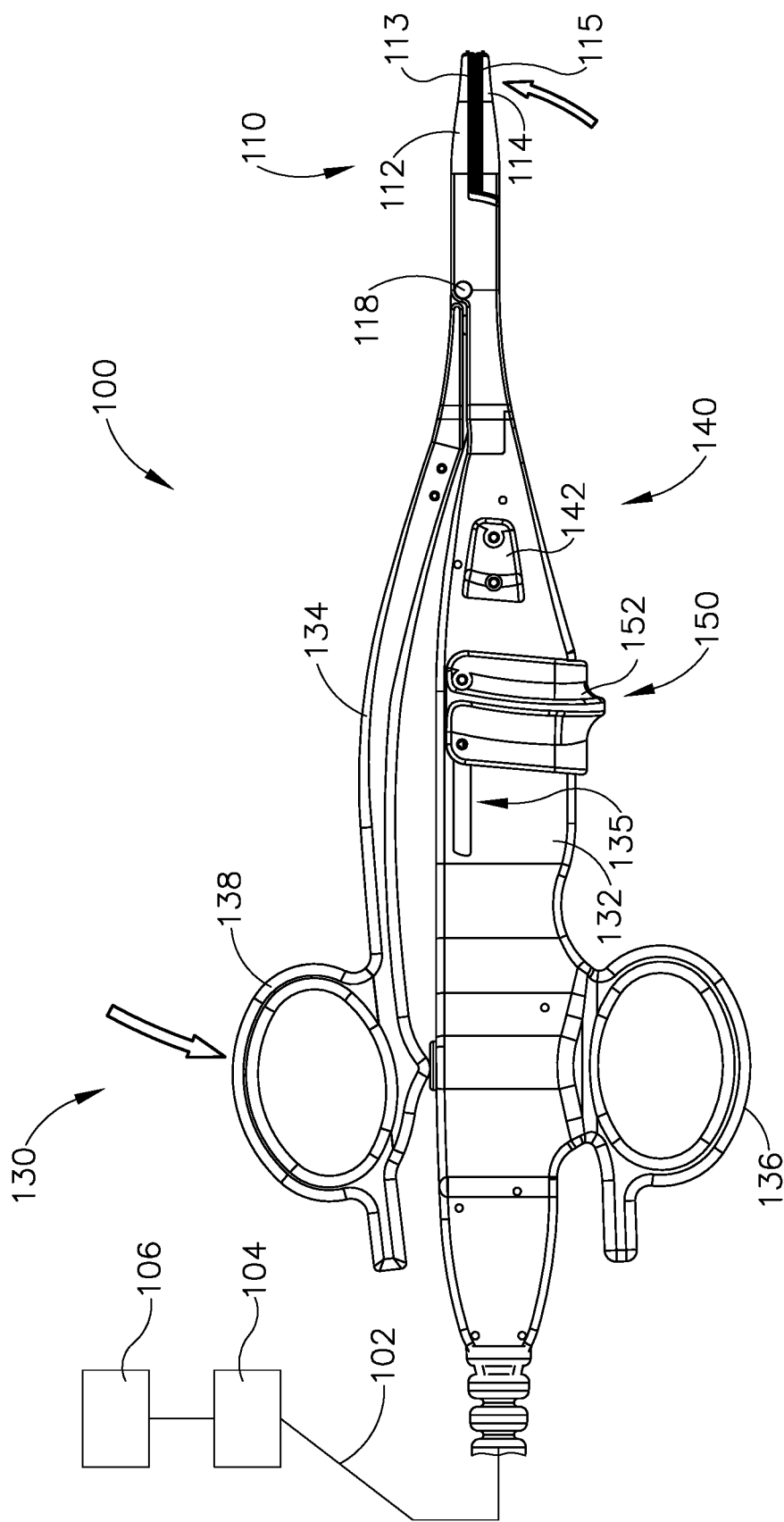
FIG. 3C depicts a side elevational view of the electrosurgical forceps instrument of FIG. 1, where the end effector is in the closed position, where the resilient arm is in a flexed position, and where the translating knife of FIG. 2 is in the proximal position.
Figure 3D:
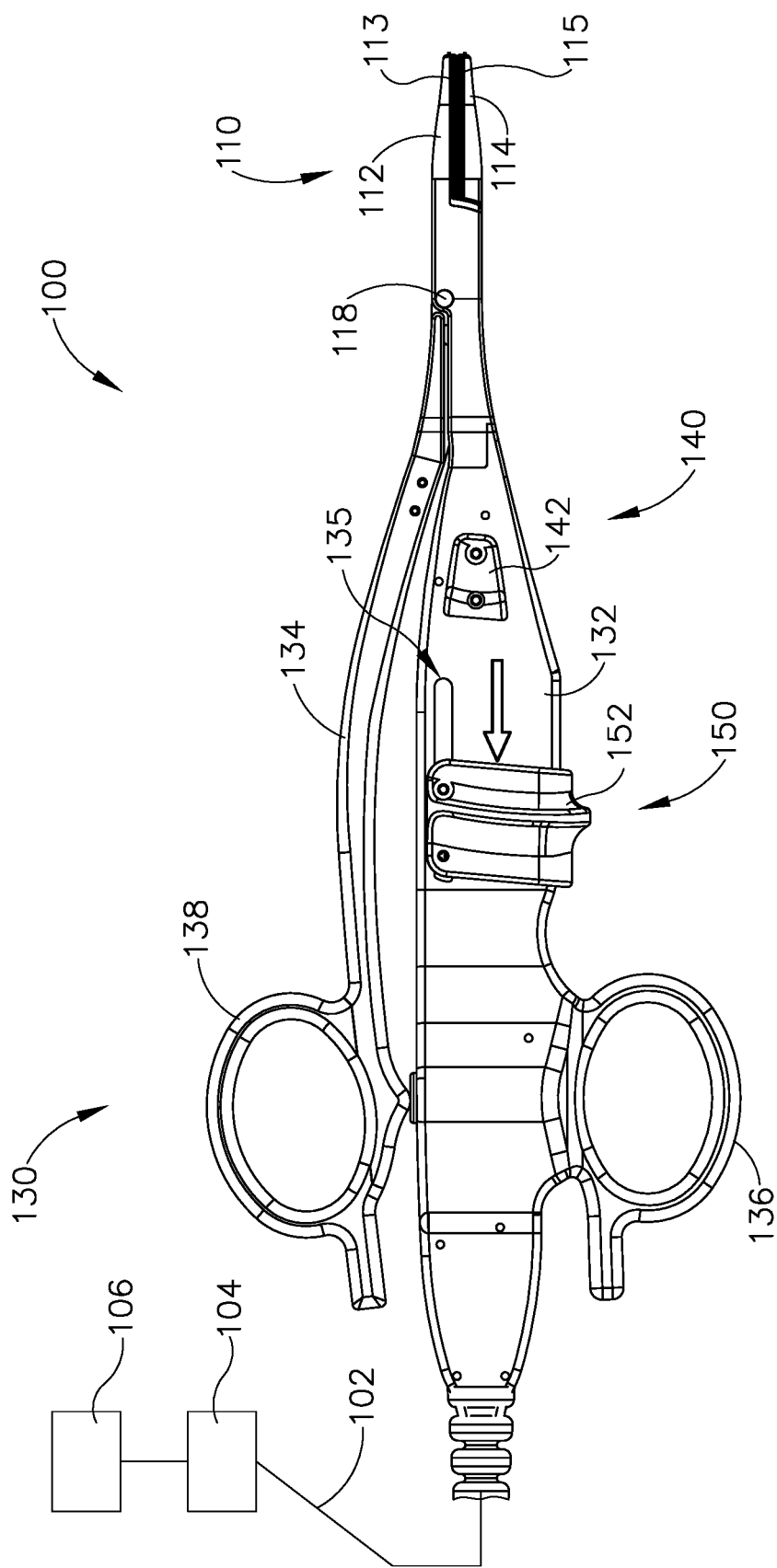
FIG. 3D depicts a side elevational view of the electrosurgical forceps instrument of FIG. 1, where the end effector is in the closed position, where the resilient arm is in the flexed position, and where the translating knife of FIG. 2 is in a distal position.

Next, as shown in FIG. 3C, if the operator desires to apply RF energy to grasped tissue, the operator may further pivot resilient arm (134) toward housing (132) such that resilient arm (134) bends to the flexed position. As this point, the closure forces imparted on tissue by jaws (112, 114) is sufficient for proper sealing. The operator may then actuate RF trigger (142) such that electrodes (113, 115) provide RF energy to grasped tissue. Next, as shown between FIGS. 3C-3D and 4A-4B, the operator may desire to sever tissue captured between jaws (112, 114). Therefore, the operator may actuate trigger (152) proximally as shown between FIGS. 3C-3D such that knife (120) actuates distally as shown between FIGS. 4A-4B. Cutting edge (122) may sever tissue captured between jaws (112, 114) as knife (120) actuates distally through elongate slot (116).

While in the current example, the operator applies RF energy to grasped tissue and then subsequently severs the tissue, the operator may alternatively sever grasped tissue first, then apply RF energy to the tissue as would be apparent to one of ordinary skill in the art in accordance with the teachings herein. Alternatively, the operator may only seal grasped tissue by applying RF energy, without severing the tissue, as would be apparent to one of ordinary skill in the art in accordance with the teachings herein. Alternately, the operator may only sever grasped tissue, without sealing the tissue, as would be apparent to one of ordinary skill in the art in accordance with the teachings herein. Alternatively, the operator may just grasp tissue, without severing or sealing the tissue, as would be apparent to one of ordinary skill in the art in accordance with the teachings herein.

II. Exemplary Alternative Electrosurgical Forceps having Thumb Ring Knife Actuator It may be desirable to prevent exposure of distal cutting edge (122) while jaws (112, 114) are in the open position. In some instances, the operator may accidentally actuate knife trigger (152) proximally while jaws (112, 114) are open, inadvertently exposing distal cutting edge (122) of knife (120) within slot (116). In other instances, the operator may begin to actuate knife trigger (152) proximally while jaws (112, 114) are initially closed then inadvertently expose distal cutting edge (122) by opening jaws (112, 114) before knife (120) returns to the pre-fired position. Inadvertent exposure of distal cutting edge (122) may cause inadvertent tissue damage. Therefore, it may be desirable to provide a mechanism that prevents actuation of knife (120) until jaws (112, 114) are sufficiently closed; and a mechanism that prevents the opening of jaws (112, 114) while knife (120) is out of the pre-fired position.

While various examples of knife actuation assemblies are described below, it should be understood various combinations or modifications may be made to such knife actuation assemblies as would be apparent to one having ordinary skill in the art in view of the teachings herein.

A. Exemplary Forceps Instrument with Thumb Ring Trigger

FIG. 5 shows an exemplary alternative electrosurgical forceps instrument (200) that may be used in replacement of instrument (100) described above. Therefore, as will be described in greater detail below, instrument (200) may be used to grasp, seal, and sever tissue. Instrument (200) includes an end effector (210), a handle assembly (230), and a firing assembly (250).

End effector (210) is substantially similar to end effector (110) described above, with differences elaborated below. End effector (210) includes a first jaw (212) having a first electrode (213), a second jaw (214) having a second electrode (215), and a knife (220) configured to translate through the first jaw (212) and the second jaw (214) in order to sever tissue. First jaw (212) and second jaw (214) are pivotably coupled with each other via pivot pin (218). First jaw (212) and second jaw (214) may pivot between an open position (FIG. 5A) and a closed position (FIG. 5B) in order to grasp tissue.

Jaws (212, 214) and electrodes (213, 215) are substantially similar to jaws (112, 114) and electrodes (113, 115) described above, respectively. First and second electrodes (213, 215) are positioned on respective jaws (212, 214) such that electrodes (213, 215) face each other when jaws (212, 214) are pivoted into the closed position. Additionally, jaws (212, 214) and electrodes (213, 215) define an elongate slot (not shown) dimensioned to slidably receive knife (220) such that knife (220) may translate from a proximal, pre-fired, position (shown in FIGS. 5A-5B) to a distal, fired, position (shown in FIG. 5C), similar to knife (120) described above. Knife (220) includes a distal cutting edge (222) configured to sever tissue captured between jaws (212, 214) in the closed position. As will be described in greater detail below, firing assembly (250) configured to decouple when jaws (212, 214) are in the open position such that knife (220) remains in the pre-fired position; while firing assembly (250) is configured to operatively couple when jaws (212, 214) are in the closed position such that the operator may fire knife (220). In other words, firing assembly (250) is rendered inoperable when jaws (212, 214) are not closed; while firing assembly (250) is rendered operable when jaws (212, 214) are in the closed position.

Similar to instrument (100) described above, handle assembly (230) may couple with control unit (104) such that control unit (104) is operable to provide RF power to electrodes (213, 215) of jaws (212, 214), to thereby seal tissue suitably captured between jaws (212, 214). Instrument (200) includes an electrode activation assembly similar to electrode activation assembly (140) described above.

Handle assembly (230) includes a housing (232) and an arm (234). Housing (232) may be substantially similar to housing (132) described above, with differences elaborated below. Housing (232) and arm (234) are pivotably coupled with each other via pivot pin (218). Housing (232) extends distally into first jaw (212), while arm (234) extends distally into second jaw (214). Housing (232) includes a finger ring (236). Housing (232) slidably houses a portion of knife (220) and firing assembly (250); while arm (234) is slidably coupled with a sliding thumb ring trigger (238) of firing assembly (250). Therefore, the operator may grasp instrument (200) in a scissor grip fashion and pivot arm (234) relative to housing (232) via rings (236, 238) in order to open and close jaws (212, 214).

Firing assembly (250) of the current example includes sliding thumb ring trigger (238), a proximal carriage (260), a beam (264), and a biasing member (268). Proximal carriage (260), beam (264), and knife (220) are all slidably disposed within housing (232). Beam (264) is coupled to both proximal carriage (260) and knife (220) such that translation of proximal carriage (260) leads to translation of knife (220). Biasing member (268) is connected to housing (232) and proximal carriage (260) such that proximal carriage (260) is biased to a proximal position associated with knife (220) in the pre-fired position. As will be described in greater detail below, proximal carriage (260) is dimensioned to receive a portion of sliding thumb ring trigger (238) such that proximal carriage (260) may couple with sliding thumb ring trigger (238) when arm (234) initially pivots jaws (212, 214) into the closed position while knife (220) is in the pre-fired position. As will also be described in greater detail below, siding thumb ring trigger (238) is configured to slide along a portion of arm (234) while trigger (238) is coupled with carriage (260) in order to actuate knife (220) between the pre-fired position and a fired position.

Figure 6:
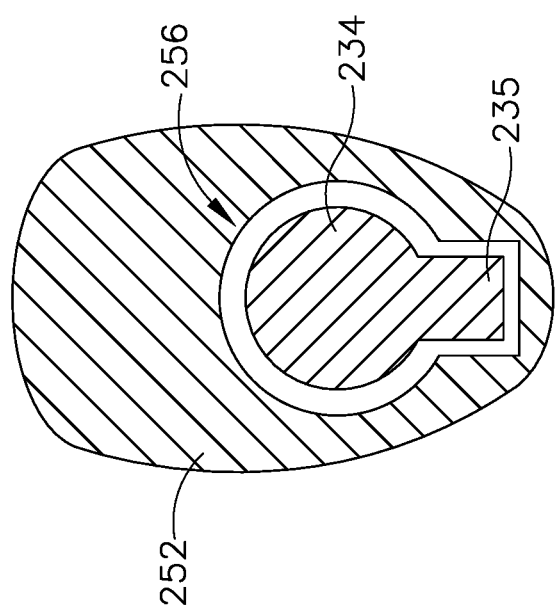
FIG. 6 depicts a cross-sectional front view of a sliding thumb trigger and an arm of the electrosurgical forceps instrument of FIG. 5A.

Sliding thumb ring trigger (238) includes an arm coupling portion (252) and a knife driving projection (254). Arm coupling portion (252) slidably couples thumb ring trigger (238) with arm (234); while knife drive projection (254) couples with proximal carriage (260) in accordance with the description herein. As best seen in FIG. 6, arm (234) includes a keyed projection (235) while arm coupling portion (252) defines a keyed opening (256). Keyed opening (256) receives arm (234) and keyed projection (235) such that sliding thumb ring trigger (238) is rotationally constrained relative to arm (234). In other words, sliding thumb ring trigger (238) may slide relative to arm (234), but may not rotate relative to arm (234).

As best seen FIGS. 7-8, a top portion of housing (232) defines a proximal opening (262) and an elongate slot (266). Proximal opening (262) has a larger lateral dimension than elongate slot (266). Elongate slot (266) includes a t-shaped profile (267). Proximal opening (262) is dimensioned to receive knife driving projection (254) as arm (234) pivots jaws (212, 214) into the closed position. Additionally, proximal carriage (260) is housed within proximal opening (262) while knife (220) is in the pre-fired position such that proximal carriage (260) receives knife driving projection (254) when arm (234) pivots jaws (212, 214) to the closed position. Therefore, since proximal carriage (260) is biased to the pre-fired position, knife driving projection (254) may selectively couple with proximal carriage (260) of firing assembly (250) when arm (234) pivots jaws (212, 214) into the closed position.

Figure 5A:
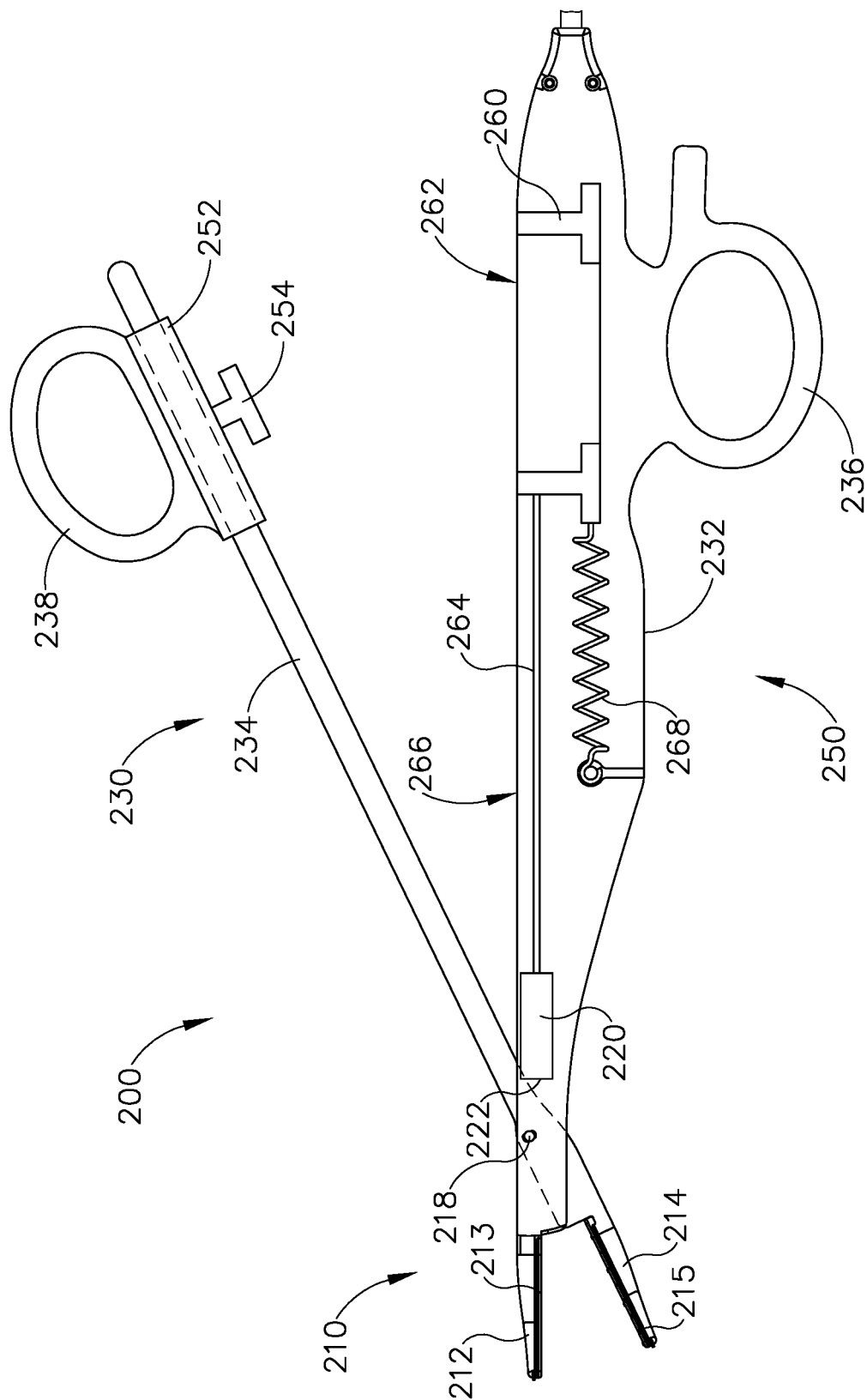
FIG. 5A depicts an elevational side view of an alternative exemplary electrosurgical forceps instrument, with some internal components show schematically, where an end effector is in an opened position, where a firing assembly is in a pre-fired position.

FIGS. 5A-5C show an exemplary use of instrument (200) in accordance with the description herein. FIG. 5A shows jaws (212, 214) in the open position with arm (234) pivoted away from housing (232) and thumb ring trigger (238) in a proximal position relative to arm (234). It should be understood that at this moment, sliding thumb ring trigger (238) relative to arm (234) will not drive knife (220) relative to jaws (212, 214). Therefore, if the operator accidentally actuates sliding thumb ring trigger (238) while jaws (212, 214) are in the open position, knife (220) will remain in the pre-fired position. If the operator desires to close jaws (212, 214) in order to grasp tissue, the operator may pivot arm (234) relative to housing (232) via rings (236, 238) to the position shown in FIG. 5B. As arm (234) pivots to the position shown in FIG. 5B, knife driving projection (254) is inserted through proximal opening (262) and within carriage (260).

As shown between FIGS. 5B-5C, when trigger (238) is coupled with proximal carriage (260) in accordance with the description herein, the operator may actuate knife (220) from the pre-fired position to a fired position by actuating sliding thumb ring trigger (238) distally. When the operator actuates sliding thumb ring trigger (238) distally, carriage (260), beam (264) and knife (220) actuates distally by overcoming the biasing force providing by biasing member (268). In particular, the operator may slide trigger (238) distally until knife (220) actuates through jaws (212, 214) in the closed position, thereby severing tissue captured between jaws (212, 214). Elongate slot (266) receives knife driving projection (254) of sliding thumb ring trigger (238) when trigger (238) is actuating distally past the pre-fired position. In particular, knife driving projection (254) is housed within the bottom portion of t-shaped profile (267) such that knife driving projection (254) and t-shaped profile (267) prevent arm (234) from pivoting away from housing (232) while knife driving projection (254) is actuated distally from proximal opening (262). Therefore, the operator may be prevented from opening jaws (212, 214) during the firing process of knife (220).

After knife (220) actuates into the fired position, the operator may release, or otherwise lessen the distal force on sliding thumb ring trigger (238), or alternatively pull proximally on thumb ring trigger (238), such that biasing member (268) drives knife (220), beam (264), carriage (260), and trigger (238) back to the pre-fired position. With trigger (238) in the pre-fired position, the operator may pivot arm (234) away from housing (232) such that jaws (212, 214) open and knife driving projection (254) exits carriage (260) and proximal opening (262). The operator may then grasp another desirable portion of tissue and repeat the process described above. It should be understood that electrodes (213, 215) may be activated at any suitable time during the exemplary use of instrument (200) described above.

Figure 10:
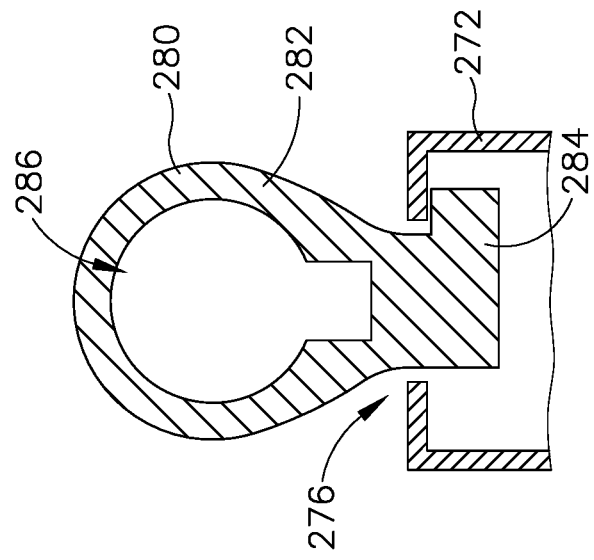
FIG. 10 depicts a cross-sectional view, taken along line 10-10 of FIG. 9, of the housing of FIG. 9 coupled with an alternative sliding thumb trigger.
Figure 9:
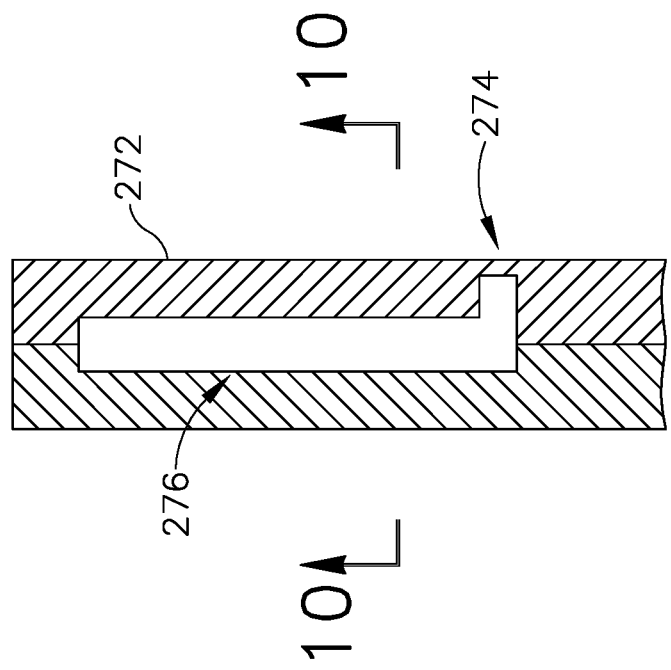
FIG. 9 depicts a top plan view of an alternative housing that may be readily incorporated into the electrosurgical forceps instrument of FIG. 5A.

While housing (232) and thumb ring trigger (238) are dimensioned to complement each other via proximal opening (262) having a circular opening and elongate slot (266) having a t-shaped profile (267), this is merely optional, as any other suitable geometric arrangement may be utilized as would be apparent to one having ordinary skill in the art in view of the teachings herein. For example, as shown in FIGS. 9-10, an alternative housing (272) and alternative thumb ring trigger (280) may be readily incorporated into instrument (200) in replacement of housing (232) and trigger (238) described above. As best seen in FIG. 9, housing (272) includes an L-shaped proximal opening (274) with corresponding elongate slot (276). As best seen in FIG. 10, trigger (280) includes an arm coupling portion (282), and an L-shaped carriage coupling portion (284). Trigger (280) defines a keyed opening (286), which is substantially similar to keyed opening (256) described above. Additionally, L-shaped carriage coupling portion (284) is configured to enter into L-shaped proximal opening (274) and slide within elongate slot (276).

B. Exemplary Auto Knife Return for Instrument with Thumb Ring Trigger

In some instances, it may be desirable to have an automatic knife return mechanism that is configured to automatically drive knife (220) to the pre-fired position after knife (220) reaches the fired position. In other words, it may be desirable to have a knife (220) that automatically returns to the pre-fired position after reaching the fired position independent of the longitudinal position of trigger (238).

FIGS. 11A-11F show an alternative firing assembly (300), an alternative arm (334), and an alternative housing (332) that may be readily incorporated into instrument (200) in replacement of firing assembly (250), arm (234), and housing (232) described above, respectively. Arm (334) is substantially similar to arm (234) described above; while housing (332) is substantially similar to housing (232) described above. As will be described in greater detail below, firing assembly (300) is configured to automatically drive knife (220) back to the pre-fired position after reaching the fired position.

Firing assembly (300) includes a sliding thumb ring trigger (301) slidably coupled with arm (334), a coupling beam (310) attached to knife (220), a transverse driving pin (312) slidably housed within coupling beam (310), and a biasing member (320) attached to coupling beam (310) and housing (332). Transverse driving pin (312) is slidably contained within a slot (316) defined by coupling beam (310), while a biasing member (314) biases transverse driving pin (312) toward one end of slot (316). Additionally, housing (332) defines a guide slot (308) extending from a proximal firing portion (306) toward a distal decoupling portion (309). Transverse driving pin (312) is at least partially contained within guide slot (308) such that transverse driving pin (312) travels along the path provided by guide slot (308). As will be described in greater detail below, guide slot (308) is configured to push transverse driving pin (312) out of engagement with sliding thumb ring trigger (301) when knife (220) reaches the fired position such that biasing member (320) automatically drives knife (220) and coupling beam (310) back toward the pre-fired position.

Sliding thumb ring trigger (301) includes an arm coupling portion (302) and a knife driving projection (304). Arm coupling portion (302) may be substantially similar to arm coupling portion (352) described above. Therefore, sliding thumb ring trigger (301) may slide relative to arm (334) while also being rotationally constrained relative to arm (334). Knife driving projection (304) is configured to actuate distally relative to arm (334) in order to abut against a transverse driving pin (312), thereby driving coupling beam (310) and knife (220) distally relative to housing (332).

FIGS. 11A-11F show an exemplary use of firing assembly (300). First, FIG. 11A shows arm (334) pivoted toward housing (332) such that jaws (212, 214) are in the closed position. Additionally, trigger (301) is in a proximal position such that knife driving projection (304) is not in contact with transverse driving pin (312). Therefore, biasing member (320) biases coupling beam (310) and knife (220) toward the pre-fired position. When the operator is ready to actuate knife (220) from the pre-fired position to the fired position, the operator may slide trigger (301) distally such that knife driving projection (304) started to contact transverse driving pin (312), as shown in FIG. 11B. At the moment shown in FIG. 11B, while knife driving projection (304) initially contacts transverse driving pin (312), knife driving projection (304) has yet to distally actuate transverse driving pin (312). Therefore, coupling beam (310) and knife (220) still remain in the pre-fired position.

Next, as shown in FIG. 11C, the operator may further actuate trigger (301) distally such that knife driving projection (304) drives transverse driving pin (312) distally along firing portion (306) of guide slot (308) defined by housing (332). In turn, transverse driving pin (312) abuts against coupling beam (310), thereby overcoming the biasing force provided by biasing member (320) to distally drive coupling beam (310) and knife (220) relative to housing (332) toward the fired position. Next, as shown in FIG. 11D, the operator may further actuate trigger (301) distally such that knife driving projection (304) drives transverse driving pin (312) with decoupling portion (309) of guide slot (308) such that pin (312) actuates downward within slot (316). At this moment, knife (220) may be in the fired position.

As shown in FIG. 11E, if the operator further actuates trigger (301) distally, knife driving projection (304) may travel distally past transverse driving pin (312) such that pin (312) and knife driving projection (304) are no longer in contact with each other. With transverse driving pin (312) no longer in contact with knife driving projection (304), there may be no external forces overcoming the biasing force of biasing member (320). Therefore, biasing member (320) may drive coupling beam (310) and knife (220) back toward the pre-fired position, even though trigger (301) remains in a distal, post-fired, position. Next, as shown in FIG. 11F, the operator may slide trigger (301) back to a proximal position such that knife driving projection (304) is proximal relative to transverse driving pin (312). In the present example, guide slot (308) does not completely surround transverse driving pin (312), such that pin (312) may vertically actuate within guide slot (308) when pin (312) is in the proximal position. Therefore, as trigger (301) slides back to the proximal position, knife driving projection (304) may push driving pin (312) downwardly such that knife driving projection (304) may travel proximally past transverse driving pin (312). Once knife driving projection (304) travels proximally past transverse driving pin (312), biasing member (314) may drive pin (312) upwardly to re-engage knife driving projection (304). Alternatively, a proximal end of guide slot (308) may have a downward recess such that knife driving projection (304) may drive pin (312) downwardly within downward recess while projection (304) actuates proximally.

With trigger (301) in the pre-fired position, the operator may pivot arm (334) away from housing (332) such that jaws (212, 214) are in the open position. The operator may then grasp another desirable portion of tissue and repeat the process described above. It should be understood that electrodes (213, 215) may be activated at any suitable time during the exemplary use of instrument (200) described above.

C. Exemplary Instrument with Latching Thumb Ring Trigger

In some instances, it may be desirable to selectively keep sliding thumb ring trigger (238) longitudinally fixed (e.g., longitudinally latched) relative to arm (234) while grasping tissue, then selectively actuate trigger (238) relative to arm (234) (e.g., longitudinally unlatched) when firing knife (220). For example, when the operator manipulates jaws (212, 214) to open and close relative to each other in order to grasp tissue, the operator may desire for sliding thumb ring trigger (238) to remain longitudinally fixed relative to arm (234) such that rings (236, 238) are easily grasped in a scissor grip fashion. If sliding thumb ring trigger (238) actuates relative to arm (234) while the operator is pivoting arm (234) relative to housing (232), it may be difficult to suitably control jaws (212, 214). Additionally, in some instances, it may be desirable to longitudinally latch trigger (238) in a proximal position associated with trigger (238) entering proximal opening (262) when jaws (212, 214) are pivoted to the closed position.

FIG. 12 shows an alternative handle assembly (340) and sliding thumb ring trigger (350) that may be readily incorporated into instrument (200) in replacement of handle assembly (230) and sliding thumb ring trigger (238) described above, respectively. Handle assembly (340) includes a housing (342) and an arm (344) pivotably coupled with each other. Housing (342) is substantially similar to housing (232) described above, with differences elaborated below. Similarly, arm (344) is substantially similar to arm (234) described above, with differences elaborated below. As will be described in greater detail below, sliding thumb ring trigger (350) and arm (344) together form a thumb ring latch assembly (360) configured to longitudinally latch trigger (350) relative to arm (344) such that thumb ring trigger (350) is fixed relative to arm (344) when the operator desires to grasp handle assembly (340) in a scissor grip fashion to open and close jaws (212, 214).

Housing (342) defines a first opening (341) and a second opening (343). First opening (341) is dimensioned to receive a knife driving projection (354) of trigger (350) such that trigger (350) may drive knife (220) from the pre-fired position to the fired position in accordance with the description herein. Second opening (343) is dimensioned to receive a proximal end (346) of arm (344) when arm (344) is pivoted toward housing (342) such that jaws (212, 214) are in the closed position. A proximal end (346) of arm (344) and corresponding portion of housing (342) include an arm latch assembly (348) that is configured to selectively latch arm (344) in the closed position relative to housing (342). Arm latch assembly (348) may be operable in any suitable manner apparent to one having ordinary skill in the art in view of the teachings herein.

Sliding thumb ring trigger (350) includes an arm coupling portion (352) and knife driving projection (354). Arm coupling portion (352) defines a keyed opening (356) substantially similar to keyed opening (256) described above, with differences elaborated below. Knife driving projection (354) may be substantially similar to knife driving projections (254, 304) described above, in accordance with the description herein. A portion of keyed opening (356) includes a latch recess (358) having an interior contact surface (359). Latch recess (358) and interior contact surface (359) form a portion of thumb ring latch assembly (360).

Arm (344) includes a resilient body (362) terminating into a contact protrusion (364). Resilient body (362) and contact protrusion (364) also form a portion of thumb ring latch assembly (360). Arm (344) defines a cutaway section (366). Resilient body (362) is sufficiently resilient such that body (362) and contact protrusion (364) may flex from a natural position (as shown in FIG. 12) to a flexed position within cutaway section (366) in response to a sufficient external force.

When in the latched configuration, as shown in FIG. 12, contact protrusion (364) may rest within latch recess (358) as to make contact with interior contact surface (359). In this particular example, resilient body (362) is in the relaxed position while in the latched configuration. However, resilient body (362) may be in a partially flexed position while in the latched configuration such that contact surface (359) and contact protrusion (364) are in constant contact with each other. Contact between protrusion (364) and interior contact surface (359) may provide a frictional braking force restricting incidental longitudinal movement of trigger (350), effetely latching trigger (350) relative to arm (344). Therefore, when in the latched position, the operator may grasp thumb ring trigger (350) and finger ring trigger of housing (342) in a scissor grip fashion to open and close jaws (212, 214) without inadvertently sliding trigger (350) relative to arm (344).

It should be understood that contact between protrusion (364) and interior contact surface (359) may restrict longitudinal movement of trigger (350) up to a predetermined force limit such that if the operator actuates trigger (350) above the predetermined force limit, interior contact surface (359) will overcome the frictional braking force. Therefore, when the operator desires to actuate trigger (350) relative to arm (344) in order to fire knife (220) in accordance with the description herein, the operator may push trigger (350) distally with sufficient force. The resilient nature of resilient body (362) may flex in response to the operator pushing trigger (350) with sufficient force such that contact between protrusion (364) and interior contact surface (359) drives resilient body (362) upward within cutaway section (366), allowing interior contact surface (359) and the rest of trigger (350) to clear protrusion (364) such that trigger (350) disassociates with interior contact surface (359). In other words, if the operator pushes trigger (350) with enough force, interior contact surface (359) may slide relative to protrusion (364) such that trigger (350) is unlatched from resilient body (362) and contact protrusion (364).

When the operator desires to slide trigger (350) back into the latched position, the operator may actuate trigger (350) proximally with sufficient force such that protrusion (364) is back within latch recess (358).

Figure 13:
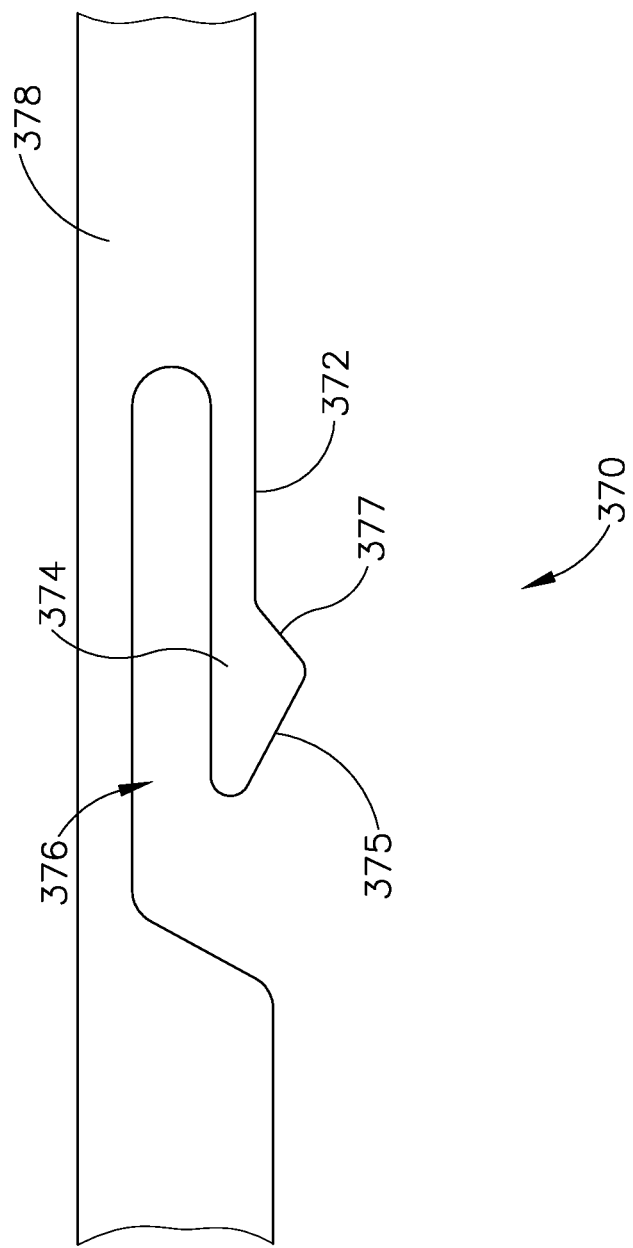
FIG. 13 depicts an elevational side view of a portion of an alternative arm that may be readily incorporated into the thumb ring latch assembly of FIG. 12.

In some instances, it may be desirable to require more force to unlatch trigger (350) from arm (344) as compared to latch trigger (350) to arm (344), or vice versa. FIG. 13 shows an alternative thumb ring latch assembly (370) providing such functionality. Thumb ring latch assembly (370) includes an alternative arm (378) that may be substantially similar to arm (344) described above, with differences elaborated below. Arm (378) includes a resilient body (372) terminating into a contact protrusion (374). Additionally, arm (378) defines a cutaway section (376). Resilient body (372) and cutaway section (376) are substantially similar to resilient body (362) and cutaway section (366) described above.

Contact protrusion (374) includes a release contact surface (377) and a return contact surface (375). Release contact surface (377) is sloped at a greater angle with a shorter distance as compared to return contact surface (375). Release contact surface (377) is configured to abut against interior contact surface (359) of trigger (350) when the operator attempts to unlatch trigger (350) from arm (378). Return contact surface (375) is configured to abut against a proximal surface defining keyed opening (356) of trigger (350) when the operator attempts to latch trigger (350) with arm (378) by proximal translation of trigger (350) relative to arm (378). Because release contact surface (377) has a greater slope and shorter distance, it may require a greater force for the operator to flex resilient body (372) due to contact between interior contact surface (359) and release contact surface (377) as compared to the force required for the operator to flex resilient body (372) due to contact between a proximal surface defining keyed opening (356) of trigger (350) and return contact surface (375). Therefore, it would require a greater external force for the operator to unlatch trigger (350) as compared to latch trigger (350). Of course, the orientation of contacts surfaces (375, 377) may be reversed such that a greater external force is required to latch trigger (350) as compared to unlatch trigger (350).

D. Exemplary Instrument with Latching Pivot Arm

In some instances, it may be desirable to latch arm (234) relative to housing (232) while arm (234) is pivoted to the position associated with jaws (212, 214) in the closed position. For instance, when the operator distally actuates sliding thumb ring trigger (238) in order to actuate knife (220) between the pre-fired position and the fired position, knife driving projection (254) may abut against portions of t-shaped profile (267) of housing (232) to prevent arm (234) from accidentally pivoting away from housing (232). However, the contact between knife driving projection (254) and t-shaped profile (267) of housing (232) may provide an undesired frictional braking force, which may inhibit actuation of trigger sliding thumb ring trigger (238), which may in turn inhibit actuation of knife (220). Therefore, it may be desirable to latch arm (234) relative to housing (232) while arm (234) is pivoted to the position associated with jaws (212, 214) in the closed position such that trigger (238) is easier to actuate.

Figure 14A:
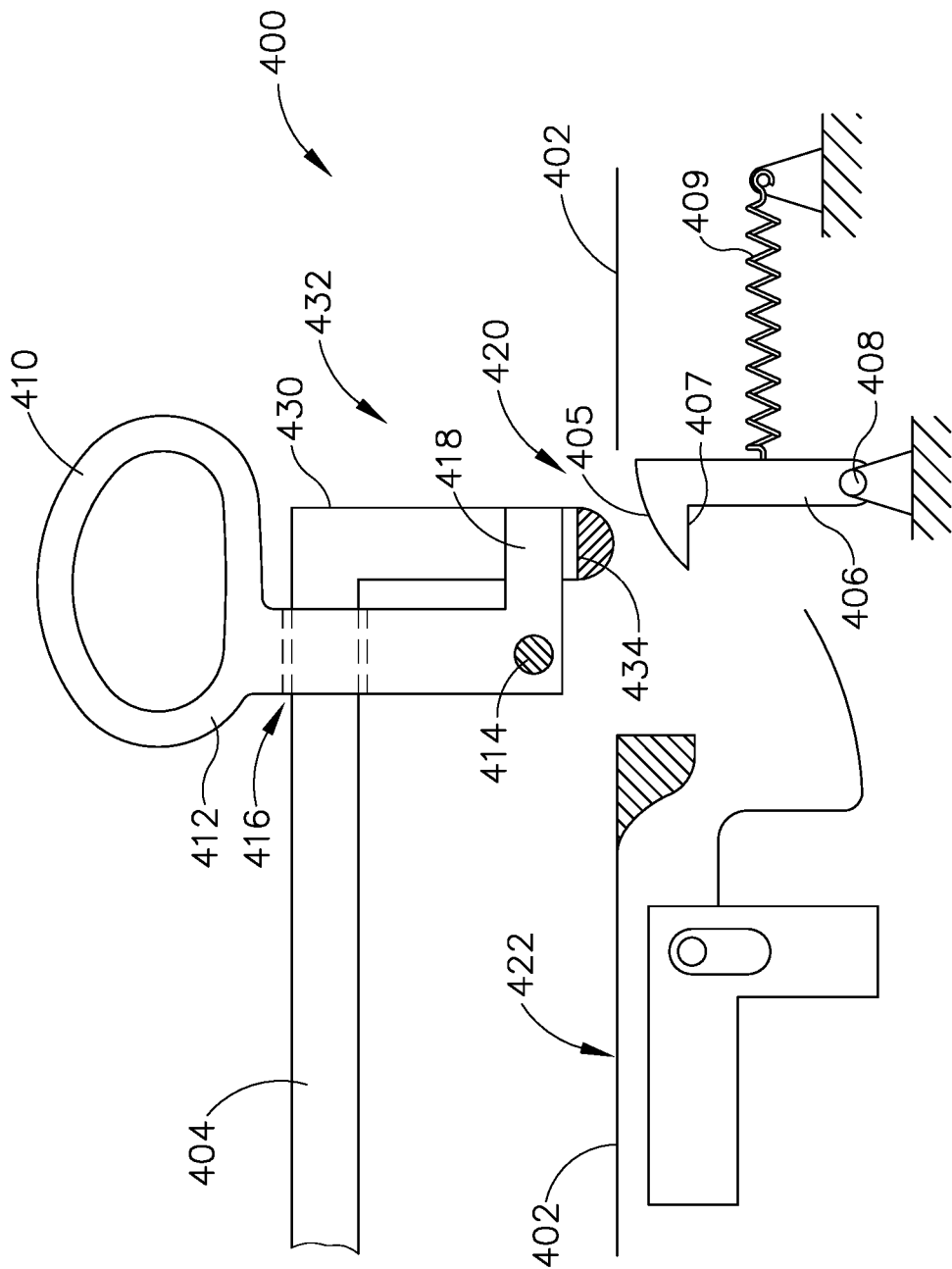
FIG. 14A depicts a side elevational view of a portion of a handle assembly having an arm latch assembly that may be readily incorporated into the electrosurgical forceps instrument of FIG. 5A, with some instrument components shown in cross-section and others shown schematically, where an arm is in an open position, where a sliding thumb ring is in a pre-fired position.
Figure 14B:
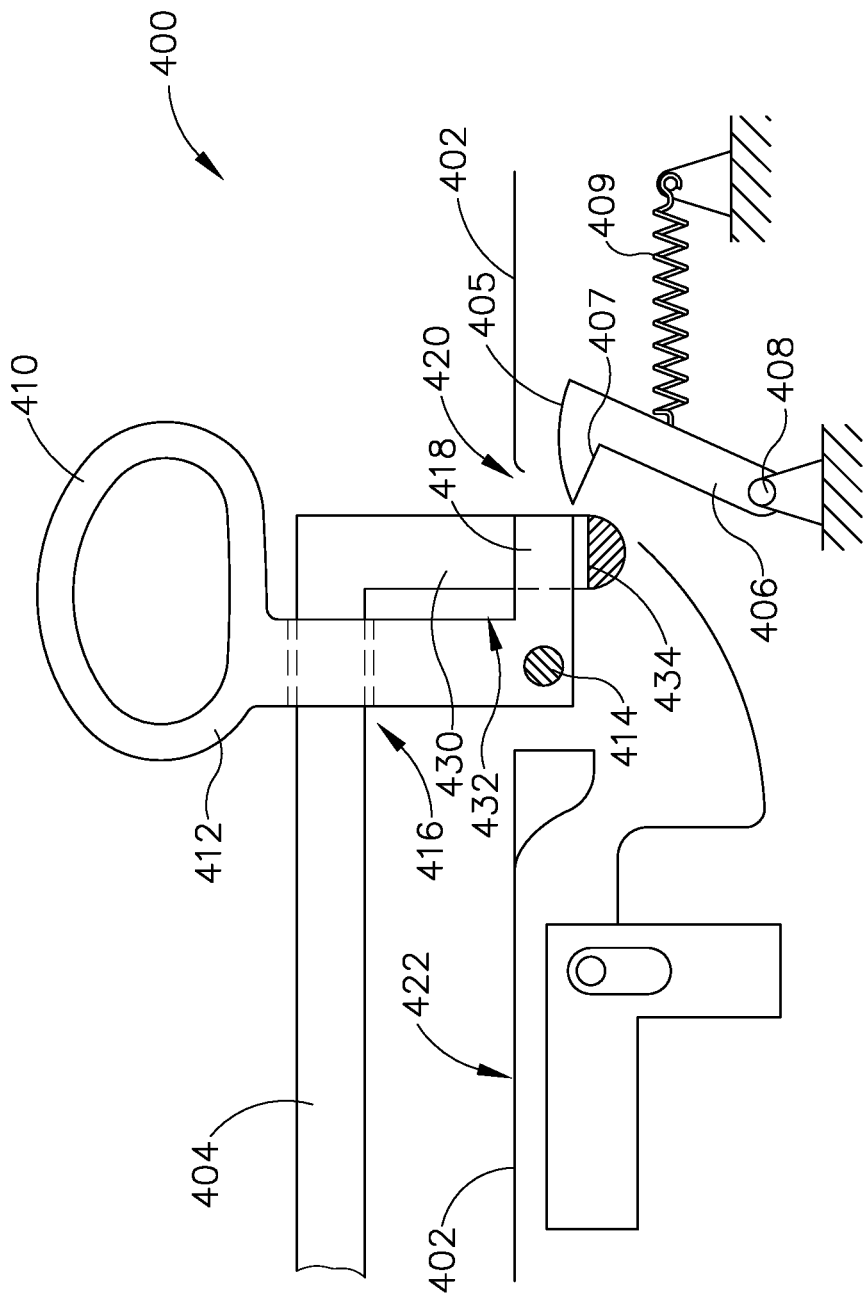
FIG. 14B depicts a side elevational view of a portion of the handle assembly and arm latch assembly of FIG. 14A, with some instrument components shown in cross-section and others shown schematically, where the arm is in a closed and unlatched position, where the sliding thumb ring is in the pre-fired position.
Figure 14C:
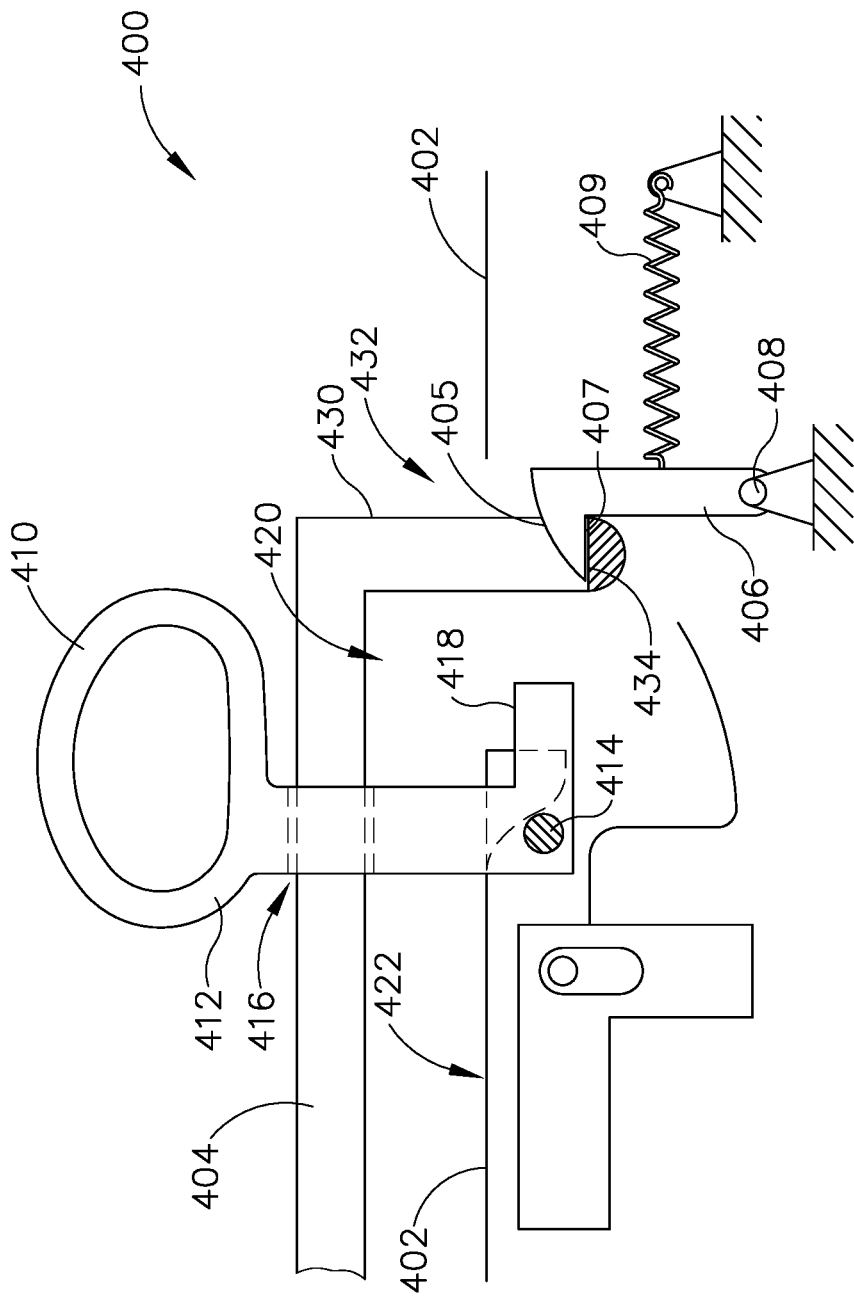
FIG. 14C depicts a side elevational view of a portion of the handle assembly and arm latch assembly of FIG. 14A, with some instrument components shown in cross-section and others shown schematically, where the arm is in a closed and latched position, where the sliding thumb ring is actuated distally toward a fired position.

FIGS. 14A-14C show an exemplary arm latch assembly (400) that may be readily incorporated into instrument (200) described above. Arm latch assembly (400) includes a housing (402), an arm (404), a sliding thumb ring trigger (410), and a pivoting latch (406). Housing (402), arm (404), and sliding thumb ring trigger (410) are substantially similar to housing (232), arm (234), and sliding thumb ring trigger (238) described above, respectively, with differences elaborated below.

Housing (402) defines a proximal opening (420) and an elongate slot (422), which may be substantially similar to proximal opening (262) and elongate slot (266) described above, respectively. Additionally, housing (402) includes a biasing member (409) that biases pivoting latch (406) to the upright position shown in FIGS. 14A and 14C. Arm (404) includes a proximal end (430) including a ledge (434) and defining an opening (432). As will be described in greater detail below, opening (432) and ledge (434) are dimension to selectively receive a portion of sliding thumb ring trigger (410) or pivoting latch (406), depending on whether arm (404) is in the unlatched or latched position.

Sliding thumb ring trigger (410) includes an arm coupling portion (412) and a knife drive projection (414). Arm coupling portion (412) may be substantially similar to arm coupling portion (252) of sliding thumb ring trigger (238) described above. Therefore, arm coupling portion (412) defines a keyed opening (416), which may be substantially similar to keyed opening (256) described above. Knife drive projection (414) may be substantially similar with knife drive projection (254) described above, with differences elaborated below. Knife drive projection (414) includes a proximally extending boss (418). As will be described in greater detail below, proximal extending boss (418) is configured to rest on ledge (434) of proximal end (430) of arm (404) when trigger (410) is in a proximal position. While proximal extending boss (418) is resting on ledge (434), pivoting latch (406) is prevented from latching arm (404) relative to housing (402).

Pivoting latch (406) is pivotably coupled with housing (402) via pivot pin (408). As mentioned above, pivoting latch (406) is biased to the upright position via biasing member (409), such as a spring. Pivoting latch (406) include a camming surface (405) and a locking surface (407). As will be described in greater detail below, camming surface (405) is configured to make contact with proximal extending boss (418) to pivot latch (406) away from the upright position, while locking surface (407) is configured to engage ledge (434) to latch arm (404) relative to housing (402).

FIGS. 14A-14C show an exemplary use of arm latch assembly (400). FIG. 14A shows arm (404) pivoted away from housing (402) such that jaws (212, 214) are at least partially open and knife driving projection (414) is out of proximal opening (420). Additionally, sliding thumb ring trigger (410) is in the proximal position such that proximal extending boss (418) is resting on ledge (434). As this moment, arm (404) is unlatched from housing (402).

Next, as shown in FIG. 14B, the operator may pivot arm (404) toward housing (402) such that jaws (212, 214) are in the closed position. At this moment, knife driving projection (414) is still resting on ledge (434). However, ledge (434) and proximal extending boss (418) make contact with camming surface (405) to pivot latch (406) away from the upright position. At the moment shown in FIG. 14B, proximally extending boss (418) prevents latch (406) from pivoting back into the upright position. At this moment, arm (404) is still in unlatched from housing (402).

Next, as shown in FIG. 14C, the operator may actuate sliding thumb ring trigger (410) in order to actuate knife (220) in accordance with the description herein. As this moment, proximal extending boss (418) no longer interferes with pivoting latch (406) such that latch (406) may pivot back to the upright position due to biasing member (409). With latch (406) in the upright position, locking surface (407) abuts against ledge (434) such that arm (404) is latched closed relative to housing (402). It should be understood that when the operator desires to unlatch arm (404), the operator may proximally actuate trigger (410) such that boss (418) pivots latch (406) away from ledge (434) (similar to that shown in FIG. 14B), then the operator may pivot arm (404) away from housing (402).

In some instances, trigger (410) may be configured to have a neutral home position slightly more distal as compared to shown in FIG. 14B such that when arm (404) is pivoted closed to housing (402), latch (406) suitably engages ledge (434). In such instances, trigger (410) may actuate from the neutral home position proximally to pivot latch (406) away from ledge (434), thereby allowing arm (404) to pivot away from housing (402). Additionally, a bias spring may be used to bias trigger (410) back to the neutral position.

Figure 15:
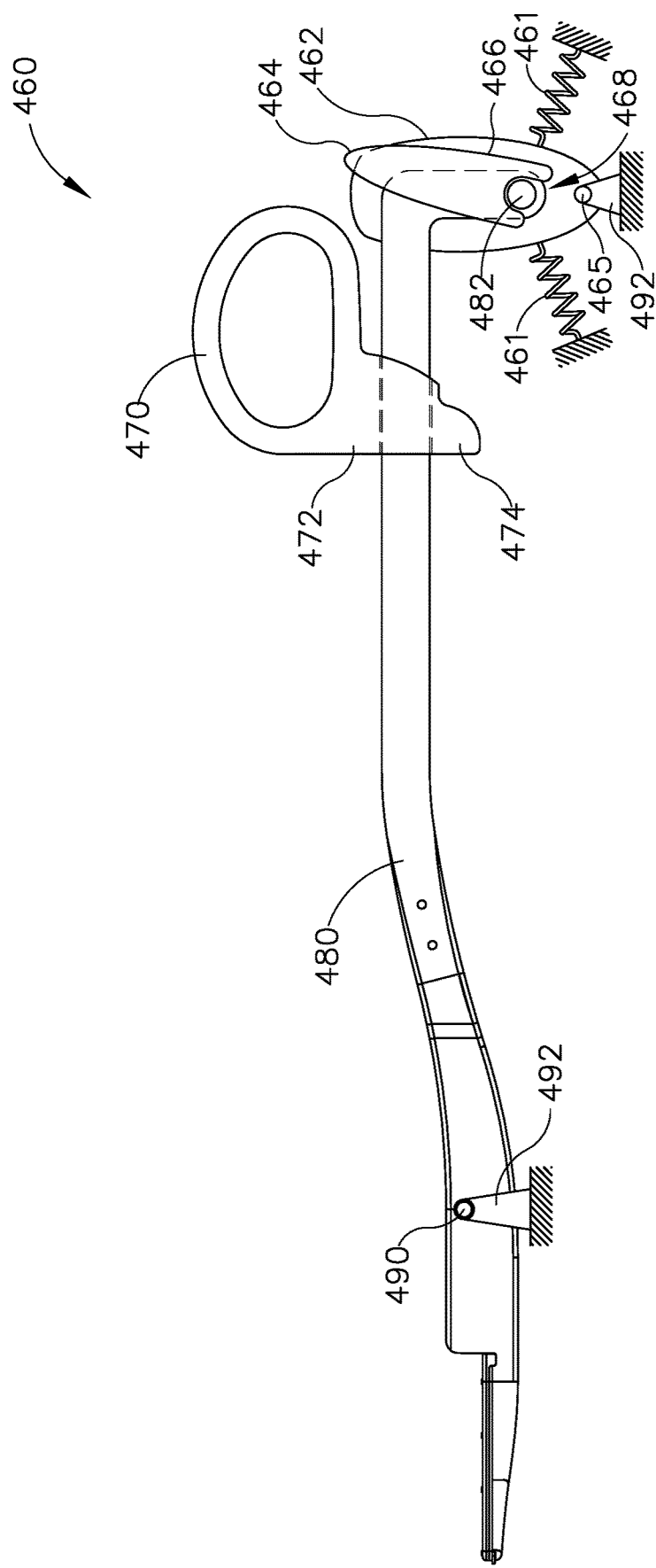
FIG. 15 depicts a side elevational view of a portion of an alternative handle assembly having an arm latch assembly that may be readily incorporated into the electrosurgical forceps instrument of FIG. 5A, with some instrument components shown in cross-section and others shown schematically, where an arm is in a latched position.

FIG. 15 shows an alternative arm latching assembly (460) that may latch arm (480) relative to housing (492) based on pivoting of arm (480) toward housing (492), rather than based on the location of a sliding thumb ring trigger (470). Latch assembly (460) includes latching body (462), an arm (480) pivotably coupled with housing (492) via pin (490), and a sliding thumb ring trigger (470). Housing (492), arm (480), and trigger (470) are substantially similar to housing (232), arm (234), and trigger (238) described above, with differences elaborated below. Therefore, trigger (470) includes an arm coupling portion (472) and a knife driving projection (474), substantially similar to arm coupling portion (252) and knife driving projection (254) described above, respectively. Arm (480) includes a latching pin (482). As will be described in greater detail below, latching pin (482) may interact with portion of latching body (462) to latch arm (480) relative to housing (492).

Latching body (462) is pivotably coupled to housing (492) via a pivot pin (465). Latching body (462) includes a lateral protrusion (464) having a camming perimeter (466). Lateral protrusion (464) also includes two legs that define a latch pocket (468), with the proximal leg extending longer than the distal leg. Latching body (462) is biased to an upright position by biasing members (461). As shown in FIG. 15, latching body (462) is pivoted proximal relative to the upright position. Latching pin (482) is configured to abut against camming perimeter (466) to drive latching body (462) about pivot pin (465) as arm (480) pivots toward hosing (492). Once latching pin (482) clears the portion of camming perimeter (466) defined by distal leg, latching body (462) may pivot back toward the upright position. However, latching pin (482) may catch the proximal leg before latching body (462) may completely pivot into the upright position. Latching pin (482) may then rest within latch pocket (468) such that arm (480) may not pivot away from housing (492). When the operator desires to unlatch arm (480) from housing (492), the operator may pivot arm (480) further toward housing (492) such latching pin (482) no longer abuts against the proximal leg, allowing biasing members (461) to pivot latching body (462) to the upright position where latch pocket (468) is not adjacent to latching pin (482). Then the operator may pivot arm (480) away from housing (492) such that latching pin (482) may be raised above latching body (462). Latching assembly may be configured similar to latching assembly described in U.S. application Ser. No. 15/989,455, entitled "Latching Clamp Arm for Electrosurgical Shears," filed May 25, 2018, issued as U.S. Pat. No. 11,039,877 on Jun. 22, 2021. The disclosure of which is incorporated by reference herein.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, and (iv) an electrode assembly configured to apply RF energy to tissue; (b) a handle assembly, wherein the handle assembly comprises: (i) a housing associated with the first jaw, and (ii) an arm associated with the second jaw, wherein the arm is configured to pivot the second jaw between the open position and the closed position; and (c) a firing assembly configured to actuate the knife between the pre-fired position and the fired position, wherein the firing assembly comprises: (i) a first body coupled with the knife, wherein the first body is slidably attached to the housing, and (ii) a second body slidably attached to the arm, wherein the second body is configured to couple with the first body when the second jaw is in the closed position, wherein the second body is configured to decouple with the first body when the second jaw is in the open position.

Example 2

The surgical instrument of Example 1, wherein the second body comprises a thumb ring.

Example 3

The surgical instrument of Example 2, wherein the thumb ring comprises an arm coupling portion.

Example 4

The surgical instrument of Example 3, wherein the arm coupling portion defines a keyed opening, wherein the arm comprises a keyed projection.

Example 5

The surgical instrument of any one or more of Examples 1 through 4, wherein the second body comprises a knife driving projection.

Example 6

The surgical instrument of Example 5, wherein the first body comprises a carriage configured to couple with the knife driving projection when the second jaw is in the closed position.

Example 7

The surgical instrument of Example 6, wherein the carriage is biased toward a proximal position.

Example 8

The surgical instrument of any one or more of Examples 5 through 7, wherein the housing defines a proximal opening dimensioned to receive the knife driving projection when the second jaw is in the closed position.

Example 9

The surgical instrument of Example 8, wherein the housing further defines an elongate slot configured to receive the knife driving projection as the firing assembly actuates the knife toward the fired position.

Example 10

The surgical instrument of any one or more of Examples 1 through 9, wherein the first body is biased to a proximal position associated with the knife in the pre-fired position.

Example 11

The surgical instrument of Example 10, wherein firing assembly further comprises a transverse driving pin associated with the first body, wherein the second body is configured to actuate the first body and the knife while the second jaw is in the closed position by contacting the transverse driving pin.

Example 12

The surgical instrument of Example 11, wherein the first body defines a slot that slidably houses the transverse driving pin.

Example 13

The surgical instrument of Example 12, wherein the housing defines a guide slot, wherein a portion of the transverse driving pin is disposed within the guide slot.

Example 14

The surgical instrument of Example 13, wherein the transverse driving pin is configured to disassociate with the second body when the knife reaches the fired position.

Example 15

The surgical instrument of Example 14, wherein the first body and the knife are configured to actuate back to the pre-fired position after the transverse driving pin disassociates with the second body.

Example 16

The surgical instrument of any one or more of Examples 1 through 15, further comprising an arm latching assembly configured to latch the arm relative to the housing.

Example 17

The surgical instrument of any one or more of Examples 1 through 16, further comprising a second body latching assembly configured to latch the second body relative to the arm.

Example 18

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, and (iv) an electrode assembly configured to apply RF energy to tissue; (b) a handle assembly, wherein the handle assembly comprises: (i) a housing associated with the first jaw, and (ii) an arm associated with the second jaw, wherein the arm is configured to pivot the second jaw between the open position and the closed position; and (c) a firing assembly configured to actuate the knife between the pre-fired position and the fired position, wherein the firing assembly comprises: (i) a coupling beam attached with the knife, wherein the coupling beam is slidably disposed within the housing, and (ii) a trigger slidably attached to the arm, wherein the trigger is operable to drive the coupling beam when the second jaw is in the closed position, wherein the trigger is inoperable to drive the coupling beam when the second jaw is not in the closed position.

Example 19

The surgical instrument of Example 18, further comprising a trigger latch configured to selectively prevent the trigger from sliding relative to the arm.

Example 20

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, and (iv) an electrode assembly configured to apply RF energy to tissue; (b) a handle assembly, wherein the handle assembly comprises: (i) a housing associated with the first jaw, and (ii) an arm associated with the second jaw, wherein the arm is configured to pivot the second jaw between the open position and the closed position; and (c) a firing assembly configured to actuate the knife between the pre-fired position and the fired position, wherein the firing assembly comprises: (i) a body slidably attached to the housing attached with the knife, wherein the body is slidably disposed within the housing, and (ii) a thumb ring slidably attached to the arm, wherein the thumb ring is configured to associate with the firing assembly when the second jaw is in the closed position such that the thumb ring may drive the body when the second jaw is in the closed position.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/989,424, entitled "Method and Apparatus for Open Electrosurgical Shears," filed May 25, 2018, issued as U.S. Pat. No. 11,020,169 on Jun. 1, 2021; U.S. application Ser. No. 15/989,430, entitled "Electrosurgical Shears with Knife Lock and Clamp-Actuated Switch," filed May 25, 2018, issued as U.S. Pat. No. 10,966,781 on Apr. 6, 2021; U.S. application Ser. No. 15/989,433, entitled "Knife Drive Assembly for Electrosurgical Shears," filed May 25, 2018, issued as U.S. Pat. No. 10,020,170 on Jun. 1, 2021; U.S. application Ser. No. 15/989,438, entitled "Knife Auto-Return Assembly for Electrosurgical Shears," filed May 25, 2018, issued as U.S. Pat. No. 10,898,259 on Jan. 26, 2021; U.S. application Ser. No. 15/989,442, entitled "Compound Screw Knife Drive for Electrosurgical Shears," filed May 25, 2018, issued as U.S. Pat. No. 10,856,931 on Dec. 8, 2020; U.S. application Ser. No. 15/989,448, entitled "Firing and Lockout Assembly for Knife for Electrosurgical Shears," filed May 25, 2018, issued as U.S. Pat. No. 11,154,346 on Oct. 26, 2021; U.S. application Ser. No. 15/989,452, entitled "Dual Stage Energy Activation for Electrosurgical Shears," filed May 25, 2018, issued as U.S. Pat. No. 11,123,129 on Sep. 21, 2021; and U.S. application Ser. No. 15/989,455, entitled "Latching Clamp Arm for Electrosurgical Shears," filed May 25, 2018, issued as U.S. Pat. No. 11,039,877 on Jun. 22, 2021. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical instrument comprising:
    (a) an end effector, wherein the end effector comprises:
        (i) a first jaw,
        (ii) a second jaw pivotably coupled with the first jaw, wherein the second jaw is operable to move between an open position and a closed position,
        (iii) a knife configured to actuate between a pre-fired position and a fired position, and
        (iv) an electrode assembly configured to apply RF energy to tissue;
    (b) a handle assembly, wherein the handle assembly comprises:
        (i) a housing associated with the first jaw, and
        (ii) an arm associated with the second jaw, wherein the arm is pivotally coupled with the housing such that the arm is configured to pivot the second jaw between the open position and the closed position; and
    (c) a firing assembly configured to actuate the knife between the pre-fired position and the fired position, wherein the firing assembly comprises:
        (i) a first body coupled with the knife, wherein the first body is slidably attached to the housing, and
        (ii) a second body slidably attached along a length of the arm such that the second body is configured to pivot with the arm relative to the housing, wherein the second body is configured to couple with the first body when the second jaw is in the closed position, wherein the second body is configured to decouple with the first body when the second jaw is in the open position, wherein the second body is configured to slide along the length of the arm when the second jaw is in the closed position in order to actuate the knife between the pre-fired position and the fired position.

2. The surgical instrument of claim 1, wherein the second body comprises a thumb ring.

3. The surgical instrument of claim 2, wherein the thumb ring comprises an arm coupling portion.

4. The surgical instrument 3, wherein the arm coupling portion defines a keyed opening, wherein the arm comprises a keyed projection.

5. The surgical instrument of claim 1, wherein the second body comprises a knife driving projection.

6. The surgical instrument of claim 5, wherein the first body comprises a carriage configured to couple with the knife driving projection when the second jaw is in the closed position.

7. The surgical instrument of claim 6, wherein the carriage is biased toward a proximal position.

8. The surgical instrument of claim 5, wherein the housing defines a proximal opening dimensioned to receive the knife driving projection when the second jaw is in the closed position.

9. The surgical instrument of claim 8, wherein the housing further defines an elongate slot configured to receive the knife driving projection as the firing assembly actuates the knife toward the fired position.

10. The surgical instrument of claim 1, wherein the first body is biased to a proximal position associated with the knife in the pre-fired position.

11. A surgical instrument comprising:
    (a) an end effector, wherein the end effector comprises:
        (i) a first jaw,
        (ii) a second jaw pivotably coupled with the first jaw, wherein the second jaw is operable to move between an open position and a closed position,
        (iii) a knife configured to actuate between a pre-fired position and a fired position, and
        (iv) an electrode assembly configured to apply RF energy to tissue;
    (b) a handle assembly, wherein the handle assembly comprises:
        (i) a housing associated with the first jaw, and
        (ii) an arm associated with the second jaw, wherein the arm is pivotally coupled with the house such that the arm is configured to pivot the second jaw between the open position and the closed position; and
    (c) a firing assembly configured to actuate the knife between the pre-fired position and the fired position, wherein the firing assembly comprises:
        (i) a coupling beam attached with the knife, wherein the coupling beam is slidably disposed within the housing, and
        (ii) a trigger slidably attached along a length of the arm such that the trigger is configured to pivot with the arm relative to the housing, wherein the trigger is operable to actuate along the length of the arm in order to drive the coupling beam when the second jaw is in the closed position, wherein the trigger is inoperable to drive the coupling beam when the second jaw is not in the closed position.

12. The surgical instrument of claim 11, further comprising a trigger latch configured to selectively prevent the trigger from sliding relative to the arm.

13. A surgical instrument comprising:
    (a) an end effector, wherein the end effector comprises:
        (i) a first jaw,
        (ii) a second jaw pivotably coupled with the first jaw, wherein the second jaw is operable to move between an open position and a closed position,
        (iii) a knife configured to actuate between a pre-fired position and a fired position, and
        (iv) an electrode assembly configured to apply RF energy to tissue;
    (b) a handle assembly, wherein the handle assembly comprises:
        (i) a housing associated with the first jaw, and
        (ii) an arm pivotally attached to the housing, wherein the arm is associated with the second jaw, wherein the arm is configured to pivot relative to the housing to thereby pivot the second jaw between the open position and the closed position; and
    (c) a firing assembly configured to actuate the knife between the pre-fired position and the fired position, wherein the firing assembly comprises:
        (i) a body slidably attached to the housing attached with the knife, wherein the body is slidably disposed within the housing, and
        (ii) a thumb ring slidably attached along a length of the arm such that the thumb ring is configured to pivot with the arm relative to the housing, wherein the thumb ring is configured to associate with the firing assembly when the second jaw is in the closed position such that the thumb ring may actuate along a path defined by the arm in order to drive the body when the second jaw is in the closed position.

\* \* \* \* \*